US012735683B2

(12) United States Patent
Paddon et al.

(10) Patent No.: US 12,735,683 B2
(45) Date of Patent: Sep. 15, 2026

(54) AMORPHA-4,11-DIENE 12-MONOOXYGENASE VARIANTS AND USES THEREOF

(71) Applicant: Amyris, Inc., Emeryville, CA (US)

(72) Inventors: Christopher J. Paddon, Emeryville, CA (US); Hanxiao Jiang, Emeryville, CA (US); Stephanie H. Kung, Emeryville, CA (US)

(73) Assignee: Amyris, Inc., Emeryville, CA (US)

( * ) Notice: Subject to any disclaimer, the term of this patent is extended or adjusted under 35 U.S.C. 154(b) by 730 days.

(21) Appl. No.: 17/794,168

(22) PCT Filed: Jan. 22, 2021

(86) PCT No.: PCT/US2021/014715

§ 371 (c)(1),
(2) Date: Jul. 20, 2022

(87) PCT Pub. No.: WO2021/150960

PCT Pub. Date: Jul. 29, 2021

(65) Prior Publication Data

US 2023/0066313 A1 Mar. 2, 2023

Related U.S. Application Data

(60) Provisional application No. 62/964,994, filed on Jan. 23, 2020.

(51) Int. Cl.

| | |
|---|---|
| ***C12N 9/02*** | (2006.01) |
| ***C12N 1/145*** | (2026.01) |
| ***C12N 15/63*** | (2006.01) |
| ***C12P 7/40*** | (2006.01) |

(52) U.S. Cl.
CPC .......... *C12N 9/0071* (2013.01); *C12N 1/145* (2021.05); *C12N 15/63* (2013.01); *C12P 7/40* (2013.01); *C12Y 114/14* (2013.01)

(58) Field of Classification Search
CPC ...... C12N 9/0071; C12N 1/145; C12N 15/63; C12P 7/40; C12Y 114/14; C12R 2001/865
See application file for complete search history.

(56) References Cited

U.S. PATENT DOCUMENTS

2016/0215301 A1 7/2016 Daviet et al.

FOREIGN PATENT DOCUMENTS

WO WO-2007/005604 A2 1/2007
WO WO-2012156976 A1 * 11/2012 .......... C12N 9/0038
WO WO-2019/090286 A2 5/2019

OTHER PUBLICATIONS

Komori et al., "Comparative functional analysis of CYP71AV1 natural variants reveals an important residue for the successive oxidation of amorpha-4,11-diene," FEBS Lett. 583(3):278-284 (Jan. 2013).
Ro et al., "Production of the antimalarial drug precursor artemisinic acid in engineered yeast," Nature. 440(7086):940-943 (Apr. 2006).
"Amorpha-4,11-diene 12-monooxygenase" UniProtKB—Q1PS23 (AMO_ARTAN), Sequence Version 2. Created Sep. 21, 2011 <https://www.uniprot.org/uniprotkb/Q1PS23/entry> (5 pages).

* cited by examiner

*Primary Examiner* — Jennifer M.H. Tichy
*Assistant Examiner* — Emily F Eix
(74) *Attorney, Agent, or Firm* — Clark & Elbing LLP

(57) ABSTRACT

Provided herein are genetically modified host cells, compositions, and methods for improved production of artemisinic acid. The host cells are genetically modified to contain a heterologous nucleic acid that expresses novel and optimized variants of *Amorpha*-4,11-diene 12-monooxygenase. Also provided herein are methods for screening for variants of cytochrome p450 enzymes that have increased enzymatic activity relative to a parental control enzyme.

12 Claims, 8 Drawing Sheets

Specification includes a Sequence Listing.

FIG. 7
No IPM
20% IPM
Art acid titer (mg/L)
2400
2200
2000
1800
1600
1400
1200
1000
800
600
400
200
0
No IPM
Y28454
20% IPM
No IPM
Y49841
20% IPM
No IPM
Y49851
20% IPM

SEQUENCE LISTING

```
<160> NUMBER OF SEQ ID NOS: 4

<210> SEQ ID NO 1
<211> LENGTH: 494
<212> TYPE: PRT
<213> ORGANISM: Artemisia annua

<400> SEQUENCE: 1

Lys Ser Ile Leu Lys Ala Met Ala Leu Ser Leu Thr Thr Ser Ile Ala
1               5                   10                  15

Leu Ala Thr Ile Leu Leu Phe Val Tyr Lys Phe Ala Thr Arg Ser Lys
            20                  25                  30

Ser Thr Lys Lys Ser Leu Pro Glu Pro Trp Arg Leu Pro Ile Ile Gly
        35                  40                  45

His Met His His Leu Ile Gly Thr Thr Pro His Arg Gly Val Arg Asp
    50                  55                  60

Leu Ala Arg Lys Tyr Gly Ser Leu Met His Leu Gln Leu Gly Glu Val
65                  70                  75                  80

Pro Thr Ile Val Val Ser Ser Pro Lys Trp Ala Lys Glu Ile Leu Thr
                85                  90                  95

Thr Tyr Asp Ile Thr Phe Ala Asn Arg Pro Glu Thr Leu Thr Gly Glu
            100                 105                 110

Ile Val Leu Tyr His Asn Thr Asp Val Val Leu Ala Pro Tyr Gly Glu
        115                 120                 125

Tyr Trp Arg Gln Leu Arg Lys Ile Cys Thr Leu Glu Leu Leu Ser Val
    130                 135                 140

Lys Lys Val Lys Ser Phe Gln Ser Leu Arg Glu Glu Glu Cys Trp Asn
145                 150                 155                 160

Leu Val Gln Glu Ile Lys Ala Ser Gly Ser Gly Arg Pro Val Asn Leu
                165                 170                 175

Ser Glu Asn Val Phe Lys Leu Ile Ala Thr Ile Leu Ser Arg Ala Ala
            180                 185                 190

Phe Gly Lys Gly Ile Lys Asp Gln Lys Glu Leu Thr Glu Ile Val Lys
        195                 200                 205

Glu Ile Leu Arg Gln Thr Gly Gly Phe Asp Val Ala Asp Ile Phe Pro
    210                 215                 220

Ser Lys Lys Phe Leu His His Leu Ser Gly Lys Arg Ala Arg Leu Thr
225                 230                 235                 240

Ser Leu Arg Lys Lys Ile Asp Asn Leu Ile Asp Asn Leu Val Ala Glu
                245                 250                 255

His Thr Val Asn Thr Ser Ser Lys Thr Asn Glu Thr Leu Leu Asp Val
            260                 265                 270

Leu Leu Arg Leu Lys Asp Ser Ala Glu Phe Pro Leu Thr Ser Asp Asn
        275                 280                 285
```

```
Ile Lys Ala Ile Ile Leu Asp Met Phe Gly Ala Gly Thr Asp Thr Ser
    290                 295                 300

Ser Ser Thr Ile Glu Trp Ala Ile Ser Glu Leu Ile Lys Cys Pro Lys
305                 310                 315                 320

Ala Met Glu Lys Val Gln Ala Glu Leu Arg Lys Ala Leu Asn Gly Lys
                325                 330                 335

Glu Lys Ile His Glu Glu Asp Ile Gln Glu Leu Ser Tyr Leu Asn Met
            340                 345                 350

Val Ile Lys Glu Thr Leu Arg Leu His Pro Pro Leu Pro Leu Val Leu
        355                 360                 365

Pro Arg Glu Cys Arg Gln Pro Val Asn Leu Ala Gly Tyr Asn Ile Pro
    370                 375                 380

Asn Lys Thr Lys Leu Ile Val Asn Val Phe Ala Ile Asn Arg Asp Pro
385                 390                 395                 400

Glu Tyr Trp Lys Asp Ala Glu Ala Phe Ile Pro Glu Arg Phe Glu Asn
                405                 410                 415

Ser Ser Ala Thr Val Met Gly Ala Glu Tyr Glu Tyr Leu Pro Phe Gly
            420                 425                 430

Ala Gly Arg Arg Met Cys Pro Gly Ala Ala Leu Gly Leu Ala Asn Val
        435                 440                 445

Gln Leu Pro Leu Ala Asn Ile Leu Tyr His Phe Asn Trp Lys Leu Pro
    450                 455                 460

Asn Gly Val Ser Tyr Asp Gln Ile Asp Met Thr Glu Ser Ser Gly Ala
465                 470                 475                 480

Thr Met Gln Arg Lys Thr Glu Leu Leu Leu Val Pro Ser Phe
                485                 490


<210> SEQ ID NO 2
<211> LENGTH: 378
<212> TYPE: PRT
<213> ORGANISM: Artemisia annua

<400> SEQUENCE: 2

Met Ala Gln Lys Ala Pro Gly Val Ile Thr Cys Lys Ala Ala Val Val
1               5                   10                  15

Trp Glu Ser Ser Gly Pro Val Val Leu Glu Glu Ile Arg Val Asp Pro
            20                  25                  30

Pro Lys Ala Ser Glu Val Arg Ile Lys Met Leu Cys Ala Ser Leu Cys
        35                  40                  45

His Thr Asp Val Leu Cys Thr Lys Gly Phe Pro Ile Pro Leu Phe Pro
    50                  55                  60

Arg Ile Pro Gly His Glu Gly Val Gly Val Ile Glu Ser Ile Gly Lys
65                  70                  75                  80

Asp Ala Lys Gly Leu Lys Pro Gly Asp Ile Val Met Pro Leu Tyr Leu
                85                  90                  95

Gly Glu Cys Gly Gln Cys Leu Asn Cys Lys Thr Gly Lys Thr Asn Leu
            100                 105                 110

Cys His Val Tyr Pro Pro Ser Phe Ser Gly Leu Met Asn Asp Gly Thr
        115                 120                 125

Ser Arg Met Ser Ile Ala Arg Thr Gly Glu Ser Ile Tyr His Phe Ala
    130                 135                 140

Ser Cys Ser Thr Trp Thr Glu Tyr Ala Val Ala Asp Cys Asn Tyr Val
145                 150                 155                 160
```

```
Leu Lys Ile Asn Pro Lys Ile Ser Tyr Pro His Ala Ser Phe Leu Ser
                165                 170                 175

Cys Gly Phe Thr Thr Gly Phe Gly Ala Thr Trp Arg Glu Thr Gln Val
            180                 185                 190

Ser Lys Gly Ser Ser Val Ala Val Phe Gly Ile Gly Thr Val Gly Leu
        195                 200                 205

Gly Val Ile Lys Gly Ala Gln Leu Gln Gly Ala Ser Lys Ile Ile Gly
    210                 215                 220

Val Asp Val Asn Gln Tyr Lys Ala Ala Lys Gly Lys Val Phe Gly Met
225                 230                 235                 240

Thr Asp Phe Ile Asn Pro Lys Asp His Pro Asp Lys Ser Val Ser Glu
                245                 250                 255

Leu Val Lys Glu Leu Thr His Gly Leu Gly Val Asp His Cys Phe Glu
            260                 265                 270

Cys Thr Gly Val Pro Ser Leu Leu Asn Glu Ala Leu Glu Ala Ser Lys
        275                 280                 285

Ile Gly Ile Gly Thr Val Val Pro Ile Gly Ala Gly Gly Glu Ala Ser
    290                 295                 300

Val Ala Ile Asn Ser Leu Ile Leu Phe Ser Gly Arg Thr Leu Lys Phe
305                 310                 315                 320

Thr Ala Phe Gly Gly Val Arg Thr Gln Ser Asp Leu Pro Val Ile Ile
                325                 330                 335

Asp Lys Cys Leu Asn Lys Glu Ile Gln Leu Asp Glu Leu Leu Thr His
            340                 345                 350

Glu Ile His Leu Asp Asn Ile Gln Glu Ala Phe Glu Ile Leu Lys Lys
        355                 360                 365

Pro Asp Cys Val Lys Ile Leu Ile Lys Phe
    370                 375


<210> SEQ ID NO 3
<211> LENGTH: 499
<212> TYPE: PRT
<213> ORGANISM: Artemisia annua

<400> SEQUENCE: 3

Met Ser Ser Gly Ala Asn Gly Ser Ser Lys Ser Ala Ser His Lys Ile
1               5                   10                  15

Lys Phe Thr Lys Leu Phe Ile Asn Gly Glu Phe Val Asp Ser Ile Ser
            20                  25                  30

Gly Asn Thr Phe Asp Thr Ile Asn Pro Ala Thr Glu Glu Val Leu Ala
        35                  40                  45

Thr Val Ala Glu Gly Arg Lys Glu Asp Ile Asp Leu Ala Val Lys Ala
    50                  55                  60

Ala Arg Glu Ala Phe Asp Asn Gly Pro Trp Pro Arg Met Ser Gly Glu
65                  70                  75                  80

Ala Arg Arg Lys Ile Met Leu Lys Phe Ala Asp Leu Ile Asp Glu Asn
                85                  90                  95

Ala Asp Glu Leu Thr Thr Leu Glu Val Ile Asp Gly Gly Lys Leu Phe
            100                 105                 110

Gly Pro Val Arg His Phe Glu Val Pro Val Ser Ser Asp Thr Phe Arg
        115                 120                 125

Tyr Phe Ala Gly Ala Ala Asp Lys Ile Arg Gly Ala Thr Leu Lys Met
    130                 135                 140
```

```
Ser Ser Asn Ile Gln Ala Tyr Thr Leu Arg Glu Pro Ile Gly Val Val
145                 150                 155                 160

Gly His Ile Ile Pro Trp Asn Gly Pro Ala Phe Met Phe Ala Thr Lys
                165                 170                 175

Val Ala Pro Ala Leu Ala Ala Gly Cys Thr Met Val Ile Lys Pro Ala
            180                 185                 190

Glu His Thr Pro Leu Thr Val Leu Phe Leu Ala His Leu Ser Lys Leu
        195                 200                 205

Ala Gly Val Pro Asp Gly Val Ile Asn Val Val Asn Gly Phe Gly Lys
    210                 215                 220

Thr Ala Gly Ala Ala Val Ser Ser His Met Asp Ile Asp Met Val Thr
225                 230                 235                 240

Phe Thr Gly Ser Thr Glu Val Gly Arg Thr Val Met Gln Ala Ala Ala
                245                 250                 255

Leu Ser Asn Leu Lys Pro Val Ser Leu Glu Leu Gly Gly Lys Ser Pro
            260                 265                 270

Leu Ile Val Phe Asp Asp Ala Asp Val Asp Lys Ala Ala Glu Phe Ala
        275                 280                 285

Ile Leu Gly Asn Phe Thr Asn Lys Gly Glu Met Cys Val Ala Gly Ser
    290                 295                 300

Arg Val Phe Val Gln Glu Gly Ile His Asp Val Phe Val Lys Lys Leu
305                 310                 315                 320

Glu Gly Ala Val Lys Ala Trp Ala Thr Arg Asp Pro Phe Asp Leu Ala
                325                 330                 335

Thr Arg His Gly Pro Gln Asn Asn Lys Gln Gln Tyr Asp Lys Val Leu
            340                 345                 350

Ser Cys Ile Asn His Gly Lys Lys Glu Gly Ala Thr Leu Val Thr Gly
        355                 360                 365

Gly Lys Pro Phe Gly Lys Lys Gly Tyr Tyr Ile Glu Pro Thr Leu Phe
    370                 375                 380

Thr Asn Val Thr Asp Asp Met Thr Ile Ala Lys Glu Glu Ile Phe Gly
385                 390                 395                 400

Pro Val Ile Ser Val Leu Lys Phe Lys Thr Val Glu Glu Val Ile Lys
                405                 410                 415

Arg Ala Asn Ala Thr Lys Tyr Gly Leu Ala Ser Gly Val Phe Thr Lys
            420                 425                 430

Asn Ile Asp Val Val Asn Thr Val Ser Arg Ser Leu Arg Ala Gly Ala
        435                 440                 445

Val Trp Val Asn Cys Tyr Leu Ala Leu Asp Arg Asp Ala Pro His Gly
    450                 455                 460

Gly Tyr Lys Met Ser Gly Phe Gly Arg Glu Gln Gly Leu Glu Ala Leu
465                 470                 475                 480

Glu His Tyr Leu Gln Ile Lys Thr Val Ala Thr Pro Ile Tyr Asp Ser
                485                 490                 495

Pro Trp Leu


<210> SEQ ID NO 4
<211> LENGTH: 546
<212> TYPE: PRT
<213> ORGANISM: Artemisia annua

<400> SEQUENCE: 4

Met Ser Leu Thr Glu Glu Lys Pro Ile Arg Pro Ile Ala Asn Phe Pro
1               5                   10                  15
```

-continued

```
Pro Ser Ile Trp Gly Asp Gln Phe Leu Ile Tyr Glu Lys Gln Val Glu
            20                  25                  30

Gln Gly Val Glu Gln Ile Val Asn Asp Leu Lys Lys Glu Val Arg Gln
        35                  40                  45

Leu Leu Lys Glu Ala Leu Asp Ile Pro Met Lys His Ala Asn Leu Leu
    50                  55                  60

Lys Leu Ile Asp Glu Ile Gln Arg Leu Gly Ile Pro Tyr His Phe Glu
65                  70                  75                  80

Arg Glu Ile Asp His Ala Leu Gln Cys Ile Tyr Glu Thr Tyr Gly Asp
                85                  90                  95

Asn Trp Asn Gly Asp Arg Ser Ser Leu Trp Phe Arg Leu Met Arg Lys
            100                 105                 110

Gln Gly Tyr Tyr Val Thr Cys Asp Val Phe Asn Asn Tyr Lys Asp Lys
        115                 120                 125

Asn Gly Ala Phe Lys Gln Ser Leu Ala Asn Asp Val Glu Gly Leu Leu
    130                 135                 140

Glu Leu Tyr Glu Ala Thr Ser Met Arg Val Pro Gly Glu Ile Ile Leu
145                 150                 155                 160

Glu Asp Ala Leu Gly Phe Thr Arg Ser Arg Leu Ser Ile Met Thr Lys
                165                 170                 175

Asp Ala Phe Ser Thr Asn Pro Ala Leu Phe Thr Glu Ile Gln Arg Ala
            180                 185                 190

Leu Lys Gln Pro Leu Trp Lys Arg Leu Pro Arg Ile Glu Ala Ala Gln
        195                 200                 205

Tyr Ile Pro Phe Tyr Gln Gln Gln Asp Ser His Asn Lys Thr Leu Leu
    210                 215                 220

Lys Leu Ala Lys Leu Glu Phe Asn Leu Leu Gln Ser Leu His Lys Glu
225                 230                 235                 240

Glu Leu Ser His Val Cys Lys Trp Trp Lys Ala Phe Asp Ile Lys Lys
                245                 250                 255

Asn Ala Pro Cys Leu Arg Asp Arg Ile Val Glu Cys Tyr Phe Trp Gly
            260                 265                 270

Leu Gly Ser Gly Tyr Glu Pro Gln Tyr Ser Arg Ala Arg Val Phe Phe
        275                 280                 285

Thr Lys Ala Val Ala Val Ile Thr Leu Ile Asp Asp Thr Tyr Asp Ala
    290                 295                 300

Tyr Gly Thr Tyr Glu Glu Leu Lys Ile Phe Thr Glu Ala Val Glu Arg
305                 310                 315                 320

Trp Ser Ile Thr Cys Leu Asp Thr Leu Pro Glu Tyr Met Lys Pro Ile
                325                 330                 335

Tyr Lys Leu Phe Met Asp Thr Tyr Thr Glu Met Glu Glu Phe Leu Ala
            340                 345                 350

Lys Glu Gly Arg Thr Asp Leu Phe Asn Cys Gly Lys Glu Phe Val Lys
        355                 360                 365

Glu Phe Val Arg Asn Leu Met Val Glu Ala Lys Trp Ala Asn Glu Gly
    370                 375                 380

His Ile Pro Thr Thr Glu Glu His Asp Pro Val Val Ile Ile Thr Gly
385                 390                 395                 400

Gly Ala Asn Leu Leu Thr Thr Thr Cys Tyr Leu Gly Met Ser Asp Ile
                405                 410                 415

Phe Thr Lys Glu Ser Val Glu Trp Ala Val Ser Ala Pro Pro Leu Phe
            420                 425                 430
```

-continued

```
Arg Tyr Ser Gly Ile Leu Gly Arg Arg Leu Asn Asp Leu Met Thr His
        435                 440                 445

Lys Ala Glu Gln Glu Arg Lys His Ser Ser Ser Ser Leu Glu Ser Tyr
    450                 455                 460

Met Lys Glu Tyr Asn Val Asn Glu Glu Tyr Ala Gln Thr Leu Ile Tyr
465                 470                 475                 480

Lys Glu Val Glu Asp Val Trp Lys Asp Ile Asn Arg Glu Tyr Leu Thr
                485                 490                 495

Thr Lys Asn Ile Pro Arg Pro Leu Leu Met Ala Val Ile Tyr Leu Cys
            500                 505                 510

Gln Phe Leu Glu Val Gln Tyr Ala Gly Lys Asp Asn Phe Thr Arg Met
        515                 520                 525

Gly Asp Glu Tyr Lys His Leu Ile Lys Ser Leu Leu Val Tyr Pro Met
    530                 535                 540

Ser Ile
545
```

AMORPHA-4,11-DIENE 12-MONOOXYGENASE VARIANTS AND USES THEREOF

SEQUENCE LISTING

The instant application contains a Sequence Listing which has been submitted electronically in ASCII format and is hereby incorporated by reference in its entirety. Said ASCII copy, created on Jul. 19, 2022, is named 51494-014002 Sequence Listing 7 19 22 ST25 and is 16,902 bytes in size.

BACKGROUND

Cytochromes p450 represent a superfamily of enzymes containing heme as a cofactor and that function as monooxygenases. In plants, the cytochrome p450 superfamily is the largest enzymatic protein family. Indeed, it has been estimated that up to 1% of a plant's genome comprises cytochrome p450-encoding genes. Members of this superfamily are involved in multiple biosynthetic and metabolic pathways and play critical roles in the synthesis of a diverse array of molecules.

The rapidly evolving field of synthetic biology involves the recombinant redesign of organisms to imbue them with novel properties or functionalities. A relatively successful application of synthetic biology is the introduction of plant-derived biosynthetic pathways into host cells, such as the yeast *Saccharomyces cerevisiae*, such that the host cells gain the ability to produce compounds normally made by the host plant. In most cases, the transplanted biosynthetic pathway requires optimization to generate recombinant host cells that produce the desired compound at commercially significant levels. This process often involves the identification and optimization of specific pathway enzymes whose suboptimal activity results in poor pathway performance and compound production. These poorly performing enzymes are bottlenecks in the biosynthetic pathway and are often optimized through iterative rounds of mutation and screening.

Cytochromes p450 obtained from plants are often bottlenecks in biosynthetic pathways imported into host cells. An example is the enzyme *Amorpha*-4,11-diene 12-monooxygenase, the wild-type version of which is rate limiting in the production of artemisinic acid in recombinant yeast. Given their prevalence in plant biosynthetic pathways, improved methods of generating and screening for optimized variant cytochromes p450 are needed.

SUMMARY OF THE INVENTION

In one aspect, the invention provides for variant *Amorpha*-4,11-diene 12-monooxygenase polypeptides having one or more amino acid substitutions relative to the amino acid sequence of SEQ ID NO:1.

In one embodiment, the one or more amino acid substitutions are selected from A8D, 194L, 194V, E128N, R172I, V219I, T240N, K244C, L333M, Q345K, L350F, T420R, A442K, A442S, Q449K, S468C, T486C, L489C, and V491 M. In another embodiment, the one or more amino acids substitutions are selected from A8D, 194V, E128N, V219I, T240N, L350F, and Q449K. In yet another embodiment, the one or more amino acid substitutions are selected from A8D, 194V, E128N, V219I, T240N, L333M, L350F, and Q449K. In a further embodiment, the one or more amino acid substitutions are selected from A8D, E128N, V219I, L350I, and Q449K. In other embodiments, the one or more amino acid substitutions are selected from A8D, E128N, V219I, L350F, and Q449K.

In an embodiment, the invention provides for a nucleic acid encoding the variant enzyme. In another embodiment, the invention provides for host cells containing the variant enzyme. In further embodiments, the host cells are capable of producing a compound selected from artemisinic alcohol, artemisinic aldehyde, and artemisinic acid. In a preferred embodiment, the host cell is capable of producing artemisinic acid. In other embodiments, the host cell contains a nucleic acid encoding a polypeptide selected from *Artemisia annua* ADH1 and *Artemisia annua* ALDH1.

In yet another aspect, the invention provides a method of generating a variant of a target p450 enzyme involving: obtaining a library of nucleic acids encoding variants of the target p450; transforming a population of host cells with the library such that each library nucleic acid is operably linked to a weak promoter; plating individual transformed host cells into individual wells of a multi-well plate; culturing the host cells under conditions that produce a test compound; measuring the level of test compound produced by the transformed host cells; and selecting variants that increase the level of the test compound relative to a control.

In an embodiment of the method, the weak promoter is selected from pGAL10, pGAL2, pGAL1_v22, pGAL1_v25, pGAL1_v2, pGAL3, and pGAL2_v22. In another embodiment of the method, the test compound is an isoprenoid. In additional embodiments of the method, the test compound is selected from hemiterpenes, monoterpenes, sesquiterpenes, diterpenes, triterpenes, sesterterpenoids, and carotenoids. In preferred embodiments of the method, the test compound is selected from artemisinic alcohol, artemisinic aldehyde, and artemisinic acid. In yet another embodiment of the method, the test compound is a meroterpenoid. In a preferred embodiment of the method, the target p450 enzyme is *Amorpha*-4,11-diene 12-monooxygenase.

In yet another embodiment, the method includes creating a second library of nucleic acids encoding variants of the target p450 enzyme, wherein the nucleic acids comprise combinations of the selected variants; transforming a population of host cells with the second library such that each second library nucleic acid is operably linked to a second weak promoter; plating individual transformed host cells into individual wells of a multi-well plate; culturing the host cells under conditions that produce the test compound; measuring the level of test compound produced in each well of the multi-well plate; and selecting second order variants that increase the level of the test compound relative to a second control.

In an embodiment of the method, the second weak promoter is distinct from the weak promoter. In another embodiment of the method, the second weak promoter is identical to the weak promoter. In a further embodiment of the method, the second control is distinct from the control. In yet another embodiment of the method, the second control is identical to the control. In a further embodiment of the method, the second library comprises nucleic acids encoding all possible combinations of the selected variants.

DETAILED DESCRIPTION OF THE INVENTION

Figure 1:
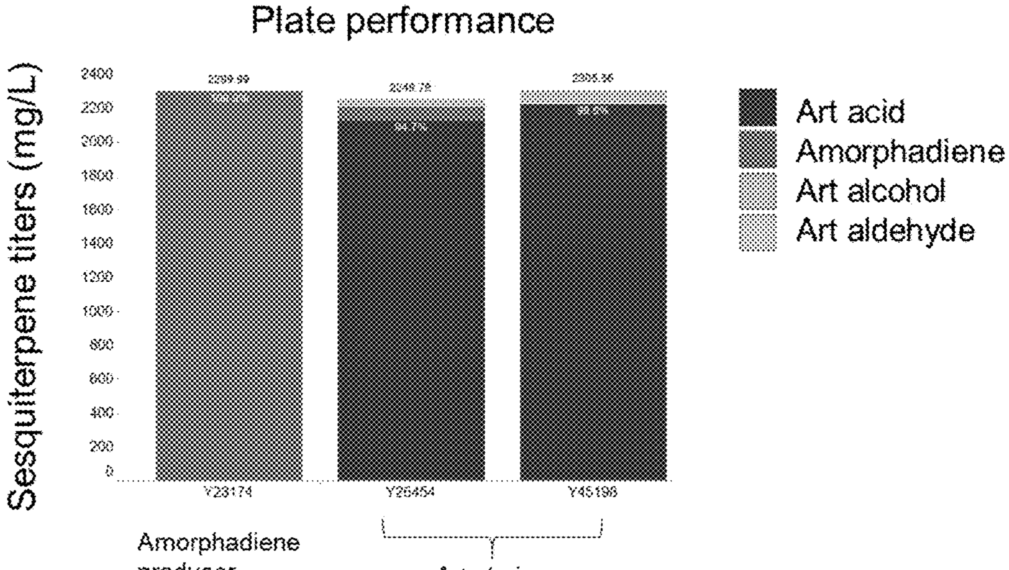
FIG. 1 is a set of graphs comparing sesquiterpene titers of artemisinic acid-producing strains grown in multi-well plates (top graph) and grown in tanks (bottom graph). In both cases, the cultures were grown in the presence of hydrophobic oil (isopropyl myristate) as described in Paddon et al. (2013, Nature 496:528-532).
Figure 1:
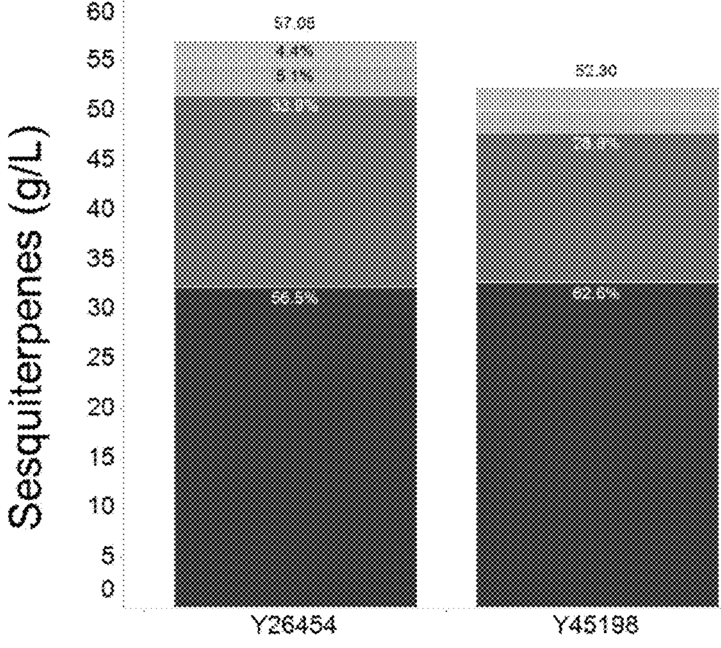

As used herein, "operably linked" refers to a juxtaposition wherein the components so described are in a relationship permitting them to function in their intended manner. For instance, a promoter is operably linked to a coding sequence if the promoter affects its transcription or expression.

As used herein, "host cell" refers to an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector that comprises a nucleotide sequence encoding one or more biosynthetic pathway gene products such as mevalonate pathway gene products), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell a heterologous nucleic acid, e.g., an exogenous nucleic acid that is foreign to the eukaryotic host cell, or a recombinant nucleic acid that is not normally found in the eukaryotic host cell.

As used herein, the term "heterologous" refers to what is not normally found in nature. The term "heterologous nucleotide sequence" refers to a nucleotide sequence not normally found in a given cell in nature. As such, a heterologous nucleotide sequence may be: (a) foreign to its host cell (i.e., is "exogenous" to the cell); (b) naturally found in the host cell (i.e., "endogenous") but present at an unnatural quantity in the cell (i.e., greater or lesser quantity than naturally found in the host cell); or (c) be naturally found in the host cell but positioned outside of its natural locus.

As used herein, the term "headroom" refers to the available additional measurable activity within a biochemical pathway, that allows for improvements in the biochemical pathway to be detected. In some instances, the activity of the biochemical pathway is evaluated by measuring the levels of one or more precursor products or the end product. Headroom in this context implies that the production of the precursors or end product have not reached a maximum such that improvements in the activity of one or more enzymes of the biochemical pathway can be detected as an increase in the one or more precursors or the end product. The invention relates to a situation where the biochemical pathway is operating at a maximum state for that growth condition (for example growth on plates) such that the pathway has no headroom and therefore any pathway variant screening cannot be carried out using that growth condition. In this situation, headroom can be restored by placing the nucleic acid encoding a pathway enzyme under control of a weak promoter, thereby reducing the measurable activity of the biochemical pathway.

As used herein, the term "variant" refers to molecules, and in particular polypeptides and polynucleotides, that differ from a specifically recited "reference" molecule in either structure or sequence. In preferred embodiments, the reference is a wild-type molecule. With respect to polypeptides and polynucleotides, variants refer to substitutions, additions, or deletions of the amino acid or nucleotide sequences, respectively.

As used herein, the term "sequence identity" or "percent identity," when used in the context of two or more polynucleotide or polypeptide sequences, refers to two or more sequences or subsequences that are the same or have a specified percentage of nucleotides or amino acid residues that are the same. For example, the sequence may have a percent identity of at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or higher identity over a specified region to a reference sequence when compared and aligned for maximum correspondence over a comparison window, or designated region as measured using a sequence comparison algorithm or by manual alignment and visual inspection. For example, percent of identity is determined by calculating the ratio of the number of identical nucleotides (or amino acid residues) in the sequence divided by the length of the total nucleotides (or amino acid residues) minus the lengths of any gaps.

For convenience, the extent of identity between two sequences can be ascertained using computer programs and mathematical algorithms known in the art. Such algorithms that calculate percent sequence identity generally account for sequence gaps and mismatches over the comparison region. Programs that compare and align sequences, like Clustal W (Thompson et al. (1994) *Nuclei Acids Res*., vol. 22, pp. 4673-4680), ALIGN (Myers et al., (1988) *CABIOS*, vol. 4, pp. 11-17), FASTA (Pearson et al., (1988) *PNAS*, vol. 85, pp. 2444-2448; Pearson (1990) *Methods Enzymol*., vol. 183, pp. 63-98), and gapped BLAST (Altschul et al., (1997) *Nucleic Acids Res*., vol. 25, pp. 3389-3402) are useful for this purpose. The BLAST or BLAST 2.0 (Altschul et al., (1990) *J. Mol. Biol*., vol. 215 pp. 403-410) are available from several sources, including the National Center for Biological Information (NCBI) and on the Internet, for use in connection with the sequence analysis programs BLASTP, BLASTN, BLASTX, TBLASTN, and TBLASTX. Additional information can be found at the NCBI web site.

In certain embodiments, the sequence alignments and percent identity calculations can be determined using the BLAST program using its standard, default parameters. For nucleotide sequence alignment and sequence identity calculations, the BLASTN program is used with its default parameters (Gap opening penalty=5, Gap extension penalty=2, Nucleic match=2, Nucleic mismatch=−3, Expectation value=10.0, Word size=11, Max matches in a query range=0). For polypeptide sequence alignment and sequence and sequence identity calculations, BLASTP program is used with its default parameters (Alignment matrix=BLOSUM62; Gap costs: Existence=11, Extension=1; Compositional adjustments=Conditional compositional score, matrix adjustment; Expectation value=10.0; Word size=6; Max matches in a query range=0). Alternatively, the following program and parameters can be used: Align Plus software of Clone Manager Suite, version 5 (Sci-Ed Software); DNA comparison: Global comparison, Standard Linear Scoring matrix, Mismatch penalty=2, Open gap penalty=4, Extend gap penalty=1. Amino acid comparison: Global comparison, BLOSUM 62 Scoring matrix. In the embodiments described herein, the sequence identity is calculated using BLASTN or BLASTP programs using their default parameters. In the embodiments described herein, the sequence alignment of two or more sequences are performed using Clustal W using the suggested default parameters (Dealign input sequences: no; Mbed-like clustering guide-tree: yes; Mbed-like clustering iteration: yes; number of combined iterations: default(0); Max guide tree iterations: default; Max HMM iterations: default; Order: input).

As used herein "*Amorpha*-4,11-diene 12-monooxygenase" is a cytochrome p450 enzyme that catalyzes three consecutive oxidations of *Amorpha*-4,11-diene to produce artemisinic acid, with artemisinic alcohol and artemisinic aldehyde as intermediate products. An illustrative example sequence for an *Amorpha*-4,11-diene 12-monooxygenase is:

```
KSILKAMALSLTTSIALATILLFVYKFATRSKSTKKSLPEPWRLPIIGH

MHHLIGTTPHRGVRDLARKYGSLMHLQLGEVPTIVVSSPKWAKEILTTYD

ITFANRPETLTGEIVLYHNTDVVLAPYGEYWRQLRKICTLELLSVKKVKS

FQSLREEECWNLVOEIKASGSGRPVNLSENVFKLIATILSRAAFGKGIKD

QKELTEIVKEILRQTGGFDVADIFPSKKFLHHLSGKRARLTSLRKKIDNL

IDNLVAEHTVNTSSKTNETLLDVLLRLKDSAEFPLTSDNIKAIILDMFGA

GTDTSSSTIEWAISELIKCPKAMEKVQAELRKALNGKEKIHEEDIQELSY

LNMVIKETLRLHPPLPLVLPRECRQPVNLAGYNIPNKTKLIVNVFAINRD

PEYWKDAEAFIPERFENSSATVMGAEYEYLPFGAGRRMCPGAALGLANVQ

LPLANILYHFNWKLPNGVSYDOIDMTESSGATMQRKTELLLVPSF.
```

As used herein "*Amorpha*-4,11-diene synthase" or "ADS" is an enzyme that catalyzes the reaction of 2-trans, 6-trans-farnesyl diphosphate to *Amorpha*-4,11-diene plus diphosphate. An illustrative example sequence of *Amorpha*-4,11-diene synthase is:

```
MSLTEEKPIR PIANFPPSIW GDQFLIYEKQ VEQGVEQIVN DLKKEVRQLL KEALDIPMKH ANLLKLIDEI

QRLGIPYHFE REIDHALQCI YETYGDNWNG DRSSLWFRLM RKQGYYVTCD VFNNYKDKNG

AFKQSLANDV EGLLELYEAT SMRVPGEIIL EDALGFTRSR LSIMTKDAFS TNPALFTEIQ

RALKQPLWKR LPRIEAAQYI PFYQQQDSHN KTLLKLAKLE FNLLQSLHKE ELSHVCKWWK

AFDIKKNAPC LRDRIVECYF WGLGSGYEPQ YSRARVFFTK AVAVITLIDD TYDAYGTYEE

LKIFTEAVER WSiTCLDTLP EYMKPIYKLF MDTYTEMEEF LAKEGRTDLF NCGKEFVKEF

VRNLMVEAKW ANEGHIPTTE EHDPVVIITG GANLLTTTCY LGMSDIFTKE SVEWAVSAPP

LFRYSGILGR RLNDLMTHKA EQERKHSSSS LESYMKEYNV NEEYAQTLIY KEVEDVWKDI

NREYLTTKNI PRPLLMAVIY LCQFLEVQYA GKDNFTRMGD EYKHLIKSLL

VYPMSI.
```

As used herein "alcohol dehydrogenase 1" or "*A. annua* alcohol dehydrogenase 1" or "ADH1" refers to an enzyme that catalyzes the conversion of artemisinic alcohol to artemisinic aldehyde. An illustrative example sequence of alcohol dehydrogenase 1 is:

```
MAQKAPGVITCKAAVVWESSGPVVLEEIRVDPPKASEVRIKMLCASLCHT

DVLCTKGFPIPLFPRIPGHEGVGVIESIGKDAKGLKPGDIVMPLYLGECG

QCLNCKTGKTNLCHVYPPSFSGLMNDGTSRMSIARTGESIYHFASCSTWT

EYAVADCNYVLKINPKISYPHASFLSCGFTTGFGATWRETQVSKGSSVAV

FGIGTVGLGVIKGAQLQGASKIIGVDVNQYKAAKGKVFGMTDFINPKDHP

DKSVSELVKELTHGLGVDHCFECTGVPSLLNEALEASKIGIGTVVPIGAG

GEASVAINSLILFSGRTLKFTAFGGVRTQSDLPVIIDKCLNKEIQLDELL

THEIHLDNIQEAFEILKKPDCVKILIKF.
```

As used herein "aldehyde dehydrogenase 1" or "*A. annua* aldehyde dehydrogenase 1" or "ALDH1" refers to an enzyme that catalyzes the NAD(P)-dependent oxidation of artemisinin precursors, artemisinic and dihydroartemisinic aldehydes, producing artemisinic acid and dihydroartemisinic acids.

An illustrative example sequence of aldehyde dehydrogenase 1 is:

```
MSSGANGSSKSASHKIKFTKLFINGEFVDSISGNTFDTINPATEEVLATV

AEGRKEDIDLAVKAAREAFDNGPWPRMSGEARRKIMLKFADLIDENADEL

TTLEVIDGGKLFGPVRHFEVPVSSDTFRYFAGAADKIRGATLKMSSNIQA

YTLREPIGVVGHIIPWNGPAFMFATKVAPALAAGCTMVIKPAEHTPLTVL

FLAHLSKLAGVPDGVINVVNGFGKTAGAAVSSHMDIDMVTFTGSTEVGRT

VMQAAALSNLKPVSLELGGKSPLIVFDDADVDKAAEFAILGNFTNKGEMC

VAGSRVFVQEGIHDVFVKKLEGAVKAWATRDPFDLATRHGPQNNKQQYDK

VLSCINHGKKEGATLVTGGKPFGKKGYYIEPTLFTNVTDDMTIAKEEIFG

PVISVLKFKTVEEVIKRANATKYGLASGVFTKNIDVVNTVSRSLRAGAVW

VNCYLALDRDAPHGGYKMSGFGREQGLEALEHYLQIKTVATPIYDSPWL
```

As used herein "target p450 enzyme" refers to a cytochrome p450 enzyme that is the object of an effort to generate optimized variants of.

As used herein "weak promoter" refers to a promoter that functions in a host cells to produce suboptimal amounts of a target p450 enzyme relative to the production of the test compound.

As used herein "test compound" refers to a compound that is either an intermediate or final product of a biosynthetic pathway involving a target p450 enzyme where the intermediate or final product is also downstream of the target p450 enzyme activity, such that measurement of the test compound is indicative of the activity of the target p450 enzyme or variants thereof.

In some embodiments, the host cells comprise one or more or all of the isoprenoid pathway enzymes selected from the group consisting of: (a) an enzyme that condenses two molecules of acetyl-coenzyme A to form acetoacetyl-CoA (e.g., an acetyl-coA thiolase); (b) an enzyme that condenses acetoacetyl-CoA with another molecule of acetyl-CoA to form 3-hydroxy-3-methylglutaryl-CoA (HMG-CoA) (e.g., an HMG-CoA synthase); (c) an enzyme that converts HMG-CoA into mevalonate (e.g., an HMG-CoA reductase); (d) an enzyme that converts mevalonate into mevalonate 5-phosphate (e.g., a mevalonate kinase); (e) an enzyme that converts mevalonate 5-phosphate into mevalonate 5-pyrophosphate (e.g., a phosphomevalonate kinase); (f) an enzyme that converts mevalonate 5-pyrophosphate into isopentenyl diphosphate (IPP) (e.g., a mevalonate pyrophosphate decarboxylase); (g) an enzyme that converts IPP into dimethylallyl pyrophosphate (DMAPP) (e.g., an IPP isomerase); (h) a polyprenyl synthase that can condense IPP and/or DMAPP molecules to form polyprenyl compounds containing more than five carbons; (i) an enzyme that condenses IPP with DMAPP to form geranyl pyrophosphate (GPP) (e.g., a GPP synthase); (j) an enzyme that condenses two molecules of IPP with one molecule of DMAPP (e.g., an FPP synthase); (k) an enzyme that condenses IPP with GPP to form farnesyl pyrophosphate (FPP) (e.g., an FPP synthase); (l) an enzyme that condenses IPP and DMAPP to form geranylgeranyl pyrophosphate (GGPP); and (m) an enzyme that condenses IPP and FPP to form GGPP.

In certain embodiments, the additional enzymes are native. In advantageous embodiments, the additional enzymes are heterologous. In certain embodiments, two or more enzymes may be combined in one polypeptide.

Cell Strains

Host cells of the invention provided herein include archae, prokaryotic, and eukaryotic cells.

Suitable prokaryotic host cells include, but are not limited to, any of a gram-positive, gran-negative, and gram-variable bacteria. Examples include, but are not limited to, cells belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphylococcus, Streptomyces, Synechococcus*, and *Zymomonas*.

Examples of prokaryotic strains include, but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei*, and *Staphylococcus aureus*. In a particular embodiment, the host cell is an *Escherichia coli* cell.

Suitable archae hosts include, but are not limited to, cells belonging to the genera: *Aeropyrum, Archaeoglobus, Halobacterium, Methanococcus, Methanobacterium, Pyrococcus, Sulfolobus*, and *Thermoplasma*. Examples of archae strains include, but are not limited to: *Archaeoglobus fulgidus, Halobacterium* sp., *Methanococcus jannaschii, Methanobacterium thermoautotrophicum, Thermoplasma acidophilum, Thermoplasma volcanium, Pyrococcus horikoshii, Pyrococcus abyssi*, and *Aeropyrum pernix*.

Suitable eukaryotic hosts include, but are not limited to, fungal cells, algal cells, insect cells, and plant cells. In some embodiments, yeasts useful in the present methods include yeasts that have been deposited with microorganism depositories (e.g. IFO, ATCC, etc.) and belong to the genera *Aciculoconidium, Ambrosiozyma, Arthroascus, Arxiozyma,*

*Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malasserzia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastoporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis*, and *Zygozyma.*

In some embodiments, the host microbe is *Saccharomyces cerevisiae, Pichia pastoris, Schizosaccharomyces pombe, Dekkera bruxellensis, Kluyveromyces lactis* (previously called *Saccharomyces lactis*), *Kluveromyces marxianus, Arxula adeninivorans*, or *Hansenula polymorpha* (now known as *Pichia angusta*). In some embodiments, the host microbe is a strain of the genus *Candida*, such as *Candida lipolytica, Candida guilliermondii, Candida krusei, Candida pseudotropicalis*, or *Candida* utils.

In preferred embodiments, the host microbe is *Saccharomyces cerevisiae*. In some embodiments, the host is a strain of *Saccharomyces cerevisiae* selected from Baker's yeast, CEN.PK2, CBS 7959, CBS 7960, CBS 7961, CBS 7962, CBS 7963, CBS 7964, IZ-1904, TA, BG-1, CR-1, SA-1, M-26, Y-904, PE-2, PE-5, VR-1 BR-1, BR-2, ME-2, VR-2, MA-3, MA-4, CAT-1, CB-1, NR-1, BT-1, and AL-1.

In some embodiments, the host microbe is a strain of *Saccharomyces cerevisiae* selected from PE-2, CAT-1, VR-1, BG-1, CR-1, and SA-1. In a particular embodiment, the strain of *Saccharomyces cerevisiae* is PE-2. In another particular embodiment, the strain of *Saccharomyces cerevisiae* is CAT-1. In another particular embodiment, the strain of *Saccharomyces cerevisiae* is BG-1.

Weak Promoters

Screening methods disclosed herein rely on the principle of reducing expression of a cytochrome p450 such that relative activity differences between the parent enzyme and variant enzymes can be detected in differences in the production of one or more test compounds. Accordingly, a weak promoter is one which when operably linked to a variant cytochrome p450 reduces expression of the enzyme and resulting enzyme activity to a suboptimal range. A suboptimal range of enzyme activity may be less than 90%, 85%, 80%, 75%, 70%, 65%, 60%, 55%, 50%, 45%, 40%, 35%, 30%, 25%, 20%, 15%, or 10% of optimal enzyme activity, i.e. the amount of activity produced using a "strong promoter", for example pGAL1. Thus, a cytochrome p450 operably linked to a weak promoter would produce less than 90%, 85%, 80%, 75%, 70%, 65%, 60%, 55%, 50%, 45%, 40%, 35%, 30%, 25%, 20%, 15%, or 10% of the test compound relative to the amount of test compound produced by a reference strong promoter, i.e. pGAL1. Table 1 presents a illustrative, non-limiting, examples of weak promoters that are useful in *Saccharomyces cerevisiae* host cells. The strength of the promoter is shown as a ratio of the activity relative to the strong promoter pGAL1.

TABLE 1

Listing of weak promoters and their activities relative to pGAL1.

| Promoters | Mean galactose GFP/pGAL1 |
|---|---|
| pGAL1 | 1 |
| pGAL1_v19 | 0.89 |
| pGAL1_v23 | 0.87 |
| pGAL1_v6 | 0.82 |
| pGAL1_v15 | 0.81 |
| pGAL1_v20 | 0.75 |
| pGAL1_v26 | 0.69 |
| pGAL1_v4 | 0.69 |
| pGAL1_v1 | 0.64 |
| pGAL10 | 0.63 |
| pGAL1_v16 | 0.61 |
| pGAL10_v6 | 0.61 |
| pGAL10_v4 | 0.6 |
| pGAL2_v5 | 0.56 |
| pGAL10_v1 | 0.54 |
| pGAL2 | 0.54 |
| pGAL1_v17 | 0.53 |
| pGAL1_v5 | 0.52 |
| pTDH3 | 0.5 |
| pGAL1_v8 | 0.5 |
| pGAL2_v7 | 0.48 |
| pGAL10_v5 | 0.45 |
| pGAL1_v22 | 0.39 |
| pGAL2_v12 | 0.37 |
| pGAL1_v10 | 0.37 |
| pGAL1_v18 | 0.36 |
| pGAL2_v1 | 0.36 |
| pGAL2_v10 | 0.36 |
| pGAL10_v10 | 0.36 |
| pGAL7 | 0.35 |
| pGAL2_v18 | 0.35 |
| pGAL2_v9 | 0.32 |
| pGAL1_v29 | 0.31 |
| pGAL10_v11 | 0.3 |
| pGAL1_v25 | 0.28 |
| pGAL2_v6 | 0.26 |
| pGAL7_v2 seamless | 0.26 |
| pGAL1_v7 | 0.25 |
| pGAL10_v7 | 0.22 |
| pGAL1_v2 | 0.21 |
| pCYC1 | 0.2 |
| pGAL1_v21 | 0.18 |
| pGAL10_v2 | 0.18 |
| pGAL2_v20 | 0.18 |
| pGAL2_v15 | 0.16 |
| pGCY1 | 0.13 |
| pGAL1_v24 | 0.13 |
| pGAL2_v3 | 0.12 |
| pGAL2_v26 | 0.12 |
| PGAL3 | 0.11 |
| pGAL1_v28 | 0.11 |
| pGAL2_v2 | 0.1 |
| pGAL2_v14 | 0.1 |
| pGAL10_v13 | 0.1 |

MEV Pathway and FPP Production

In some embodiments, a genetically modified host cell provided herein comprises one or more heterologous enzymes of the MEV pathway, useful for the formation of FPP. The one or more enzymes of the MEV pathway may include an enzyme that condenses acetyl-CoA with malonyl-CoA to form acetoacetyl-CoA; an enzyme that condenses two molecules of acetyl-CoA to form acetoacetyl-CoA; an enzyme that condenses acetoacetyl-CoA with acetyl-CoA to form HMG-CoA; or an enzyme that converts HMG-CoA to mevalonate. In addition, the genetically modified host cells may include a MEV pathway enzyme that phosphorylates mevalonate to mevalonate 5-phosphate; a MEV pathway enzyme that converts mevalonate 5-phosphate to mevalonate 5-pyrophosphate; a MEV pathway enzyme that converts mevalonate 5-pyrophosphate to isopentenyl pyrophosphate; or a MEV pathway enzyme that converts isopentenyl pyrophosphate to dimethylallyl diphosphate. In particular, the one or more enzymes of the MEV pathway are selected from acetyl-CoA thiolase, acetoacetyl-CoA synthetase, HMG-CoA synthase, HMG-CoA reductase, mevalonate kinase, phosphomevalonate kinase, mevalonate pyrophosphate decarboxylase, and isopentyl diphosphate:dimethylallyl diphosphate isomerase (IDI or IPP isomerase). The genetically modified host cell of the invention may express one or more of the heterologous enzymes of the MEV from one or more heterologous nucleotide sequences comprising the coding sequence of the one or more MEV pathway enzymes.

In some embodiments, the genetically modified host cell comprises a heterologous nucleic acid encoding an enzyme that can convert isopentenyl pyrophosphate (IPP) into dimethylallyl pyrophosphate (DMAPP). In addition, the host cell may contain a heterologous nucleic acid encoding an enzyme that may condense IPP and/or DMAPP molecules to form a polyprenyl compound. In some embodiments, the genetically modified host cell further contains a heterologous nucleic acid encoding an enzyme that may modify IPP or a polyprenyl to form an isoprenoid compound, such as FPP.

Conversion of Acetyl-CoA to Acetoacetyl-CoA The genetically modified host cell may contain a heterologous nucleic acid that encodes an enzyme that may condense two molecules of acetyl-coenzyme A to form acetoacetyl-CoA (an acetyl-CoA thiolase). Examples of nucleotide sequences encoding acetyl-CoA thiolase include (accession no. NC_000913 REGION: 2324131.2325315 (*Escherichia coli*)); (D49362 (*Paracoccus denitrificans*)); and (L20428 (*Saccharomyces cerevisiae*)).

Acetyl-CoA thiolase catalyzes the reversible condensation of two molecules of acetyl-CoA to yield acetoacetyl-CoA, but this reaction is thermodynamically unfavorable; acetoacetyl-CoA thiolysis is favored over acetoacetyl-CoA synthesis. Acetoacetyl-CoA synthase (AACS) (also referred to as acetyl-CoA:malonyl-CoA acyltransferase; EC 2.3.1.194) condenses acetyl-CoA with malonyl-CoA to form acetoacetyl-CoA. In contrast to acetyl-CoA thiolase, AACS-catalyzed acetoacetyl-CoA synthesis is essentially an energy-favored reaction, due to the associated decarboxylation of malonyl-CoA. In addition, AACS exhibits no thiolysis activity against acetoacetyl-CoA, and thus the reaction is irreversible.

In cells expressing acetyl-CoA thiolase and a heterologous ADA and/or phosphotransacetylase (PTA), the reversible reaction catalyzed by acetyl-CoA thiolase, which favors acetoacetyl-CoA thiolysis, may result in a large acetyl-CoA pool. In view of the reversible activity of ADA, this acetyl-CoA pool may in turn drive ADA towards the reverse reaction of converting acetyl-CoA to acetaldehyde, thereby diminishing the benefits provided by ADA towards acetyl-CoA production. Similarly, the activity of PTA is reversible, and thus, a large acetyl-CoA pool may drive PTA towards the reverse reaction of converting acetyl-CoA to acetyl phosphate. Therefore, in some embodiments, in order to provide a strong pull on acetyl-CoA to drive the forward reaction of ADA and PTA, the MEV pathway of the genetically modified host cell provided herein utilizes an acetoacetyl-CoA synthase to form acetoacetyl-CoA from acetyl-CoA and malonyl-CoA.

The AACS obtained from *Streptomyces* sp. Strain CL190 may be used (see Okamura et al., (2010), PNAS, vol. 107, pp. 11265-11270). Representative AACS encoding nucleic acids sequences from *Streptomyces* sp. Strain CL190 include the sequence of accession no. AB540131.1, and the corresponding AACS protein sequences include the sequence of accession nos. D7URV0 and BAJ10048. Other acetoacetyl-CoA synthases useful for the invention include those of *Streptomyces* sp. (see accession nos. AB183750; KO-3988 BAD86806; KO-3988 AB212624; and KO-2988 BAE78983); *S. anulatus* strain 9663 (see accession nos. FN178498 and CAX48662); Actinoplanes sp. A40644 (see accession nos. AB113568 and BAD07381); *Streptomyces* sp. C (see accession nos. NZ_ACEW010000640 and ZP_05511702); Nocardiopsis dassonvillei DSM 43111 (see accession nos. NZ_ABUI01000023 and ZP_04335288); *Mycobacterium ulcerans* Agy99 (see accession nos. NC_008611 and YP_907152); *Mycobacterium marinum* M (see accession nos. NC_010612 and YP_001851502); *Streptomyces* sp. Mg1 (see accession nos. NZ_DS570501 and ZP_05002626); *Streptomyces* sp. AA4 (see accession nos. NZ_ACEV01000037 and ZP_05478992); *S. roseosporus* NRRL 15998 (see accession nos. NZ_ABYB01000295 and ZP_04696763); *Streptomyces* sp. ACTE (see accession nos. NZ_ADFD01000030 and ZP_06275834); *S. viridochromogenes* DSM 40736 (see accession nos. NZ_ACEZ01000031 and ZP_05529691); *Frankia* sp. Cc13 (see accession nos. NC_007777 and YP_480101); *Nocardia brasiliensis* (see accession nos. NC_018681 and YP_006812440.1); and *Austwickia chelonae* (see accession nos. NZ_BAGZ01000005 and ZP_10950493.1). Additional suitable acetoacetyl-CoA synthases include those described in U.S. Patent Application Publication Nos. 2010/0285549 and 2011/0281315.

Acetoacetyl-CoA synthases also useful in the compositions and methods provided herein include those molecules which are said to be "derivatives" of any of the acetoacetyl-CoA synthases described herein. Such a "derivative" has the following characteristics: (1) it shares substantial homology with any of the acetoacetyl-CoA synthases described herein; and (2) is capable of catalyzing the irreversible condensation of acetyl-CoA with malonyl-CoA to form acetoacetyl-CoA. A derivative of an acetoacetyl-CoA synthase is said to share "substantial homology" with acetoacetyl-CoA synthase if the amino acid sequences of the derivative is at least 80%, and more preferably at least 90%, and most preferably at least 95%, the same as that of acetoacetyl-CoA synthase.

Conversion of Acetoacetyl-CoA to HMG-CoA

In some embodiments, the host cell comprises a heterologous nucleotide sequence encoding an enzyme that can condense acetoacetyl-CoA with another molecule of acetyl-CoA to form 3-hydroxy-3-methylglutaryl-CoA (HMG-CoA), e.g., a HMG-CoA synthase. Examples of nucleotide sequences encoding such an enzyme include: (NC_001145. complement 19061.20536; *Saccharomyces cerevisiae*), (X96617; *Saccharomyces cerevisiae*), (X83882; *Arabidopsis thaliana*), (AB037907; Kitasatospora griseola), (BT007302; *Homo sapiens*), and (NC_002758, Locus tag SAV2546, GeneID 1122571; *Staphylococcus aureus*).

Conversion of HMG-CoA to Mevalonate

In some embodiments, the host cell comprises a heterologous nucleotide sequence encoding an enzyme that can convert HMG-CoA into mevalonate, e.g., a HMG-CoA reductase. The HMG-CoA reductase may be an NADH-using hydroxymethylglutaryl-CoA reductase-CoA reductase. HMG-CoA reductases (EC 1.1.1.34; EC 1.1.1.88) catalyze the reductive deacylation of (S)-HMG-CoA to (R)-mevalonate, and can be categorized into two classes, class I and class II HMGrs. Class I includes the enzymes from eukaryotes and most archaea, and class II includes the HMG-CoA reductases of certain prokaryotes and archaea. In addition to the divergence in the sequences, the enzymes of the two classes also differ with regard to their cofactor specificity. Unlike the class I enzymes, which utilize NADPH exclusively, the class II HMG-CoA reductases vary in the ability to discriminate between NADPH and NADH (See, e.g., Hedl et al., (2004) *Journal of Bacteriology*, vol. 186, pp. 1927-1932).

HMG-CoA reductases useful for the invention include HMG-CoA reductases that are capable of utilizing NADH as a cofactor, e.g., HMG-CoA reductase from *P. mevalonii, A. fulgidus*, or *S. aureus*. In particular embodiments, the HMG-CoA reductase is capable of only utilizing NADH as a cofactor, e.g., HMG-CoA reductase from *P. mevalonii, S. pomeroyi*, or *D. acidovorans.*

In some embodiments, the NADH-using HMG-CoA reductase is from *Pseudomonas mevalonii*. The sequence of the wild-type mvaA gene of *Pseudomonas mevalonii*, which encodes HMG-CoA reductase (EC 1.1.1.88), has been previously described (see Beach and Rodwell, (1989), *J. Bacteriol.*, vol. 171, pp. 2994-3001). Representative mvaA nucleotide sequences of *Pseudomonas mevalonii* include accession number M24015. Representative HMG-CoA reductase protein sequences of *Pseudomonas mevalonii* include accession numbers AAA25837, P13702, MVAA_PSEMV.

In some embodiments, the NADH-using HMG-CoA reductase is from *Silicibacter pomeroyi*. Representative HMG-CoA reductase nucleotide sequences of *Silicibacter pomeroyi* include accession number NC_006569.1. Representative HMG-CoA reductase protein sequences of *Silicibacter pomeroyi* include accession number YP_164994.

In some embodiments, the NADH-using HMG-CoA reductase is from *Delftia acidovorans*. A representative HMG-CoA reductase nucleotide sequences of *Delftia acidovorans* includes NC_010002 REGION: complement (319980 . . . 321269). Representative HMG-CoA reductase protein sequences of *Delftia acidovorans* include accession number YP_001561318.

In some embodiments, the NADH-using HMG-CoA reductase is from *Solanum tuberosum* (see Crane et al., (2002), *J. Plant Physiol*., vol. 159, pp. 1301-1307).

NADH-using HMG-CoA reductases useful in the practice of the invention also include those molecules which are said to be "derivatives" of any of the NADH-using HMG-CoA reductases described herein, e.g., from *P. mevalonii, S. pomeroyi* and *D. acidovorans*. Such a "derivative" has the following characteristics: (1) it shares substantial homology with any of the NADH-using HMG-CoA reductases described herein; and (2) is capable of catalyzing the reductive deacylation of (S)-HMG-CoA to (R)-mevalonate while preferentially using NADH as a cofactor. A derivative of an NADH-using HMG-CoA reductase is said to share "substantial homology" with NADH-using HMG-CoA reductase if the amino acid sequences of the derivative is at least 80%, and more preferably at least 90%, and most preferably at least 95%, the same as that of NADH-using HMG-CoA reductase.

As used herein, the phrase "NADH-using" means that the NADH-using HMG-CoA reductase is selective for NADH over NADPH as a cofactor, for example, by demonstrating a higher specific activity for NADH than for NADPH. The selectivity for NADH as a cofactor is expressed as a $k_{cat}^{(NADH)}/k_{cat}^{(NADPH)}$ ratio. The NADH-using HMG-CoA reductase of the invention may have a $k_{cat}^{(NADH)}/k_{cat}^{(NADPH)}$ ratio of at least 5, 10, 15, 20, 25 or greater than 25. The NADH-using HMG-CoA reductase may use NADH exclusively. For example, an NADH-using HMG-CoA reductase that uses NADH exclusively displays some activity with NADH supplied as the sole cofactor in vitro, and displays no detectable activity when NADPH is supplied as the sole cofactor. Any method for determining cofactor specificity known in the art can be utilized to identify HMG-CoA reductases having a preference for NADH as cofactor (see e.g., (Kim et al., (2000), *Protein Science*, vol. 9, pp. 1226-1234) and (Wilding et al., (2000), *J. Bacteriol*., vol. 182, pp. 5147-5152).

In some cases, the NADH-using HMG-CoA reductase is engineered to be selective for NADH over NAPDH, for example, through site-directed mutagenesis of the cofactor-binding pocket. Methods for engineering NADH-selectivity are described in Watanabe et al., (2007), Microbiology, vol. 153, pp. 3044-3054), and methods for determining the cofactor specificity of HMG-CoA reductases are described in Kim et al., (2000), *Protein Sci*., vol. 9, pp. 1226-1234).

The NADH-using HMG-CoA reductase may be derived from a host species that natively comprises a mevalonate degradative pathway, for example, a host species that catabolizes mevalonate as its sole carbon source. In these cases, the NADH-using HMG-CoA reductase, which normally catalyzes the oxidative acylation of internalized (R)-mevalonate to (S)-HMG-CoA within its native host cell, is utilized to catalyze the reverse reaction, that is, the reductive deacylation of (S)-HMG-CoA to (R)-mevalonate, in a genetically modified host cell comprising a mevalonate biosynthetic pathway. Prokaryotes capable of growth on mevalonate as their sole carbon source have been described by: (Anderson et al., (1989), *J. Bacteriol*, vol. 171, pp. 6468-6472); (Beach et al., (1989), *J. Bacteriol*., vol. 171, pp. 2994-3001); Bensch et al., *J. Biol. Chem*., vol. 245, pp. 3755-3762); (Fimongnari et al., (1965), *Biochemistry*, vol. 4, pp. 2086-2090); Siddiqi et al., (1962), *Biochem. Biophys. Res. Commun*., vol. 8, pp. 110-113); (Siddiqi et al., (1967), *J. Bacteriol*., vol. 93, pp. 207-214); and (Takatsuji et al., (1983), *Biochem. Biophys. Res. Commun*., vol. 110, pp. 187-193).

The host cell may contain both a NADH-using HMGr and an NADPH-using HMG-CoA reductase. Examples of nucleotide sequences encoding an NADPH-using HMG-CoA reductase include: (NM_206548; *Drosophila melanogaster*), (NC_002758, Locus tag SAV2545, GeneID 1122570; *Staphylococcus aureus*), (AB015627; *Streptomyces* sp. KO 3988), (AX128213, providing the sequence encoding a truncated HMG-CoA reductase; *Saccharomyces cerevisiae*), and (NC_001145: complement (115734.118898; *Saccharomyces cerevisiae*).

Conversion of Mevalonate to Mevalonate-5-Phosphate

The host cell may contain a heterologous nucleotide sequence encoding an enzyme that can convert mevalonate into mevalonate 5-phosphate, e.g., a mevalonate kinase. Illustrative examples of nucleotide sequences encoding such an enzyme include: (L77688; *Arabidopsis thaliana*) and (X55875; *Saccharomyces cerevisiae*).

Conversion of Mevalonate-5-Phosphate to Mevalonate-5-Pyrophosphate

The host cell may contain a heterologous nucleotide sequence encoding an enzyme that can convert mevalonate 5-phosphate into mevalonate 5-pyrophosphate, e.g., a phosphomevalonate kinase. Illustrative examples of nucleotide sequences encoding such an enzyme include: (AF429385;

Hevea *brasiliensis*), (NM_006556; *Homo sapiens*), and (NC_001145. complement 712315.713670; *Saccharomyces cerevisiae*).

Conversion of Mevalonate-5-Pyrophosphate to IPP

The host cell may contain a heterologous nucleotide sequence encoding an enzyme that can convert mevalonate 5-pyrophosphate into isopentenyl diphosphate (IPP), e.g., a mevalonate pyrophosphate decarboxylase. Illustrative examples of nucleotide sequences encoding such an enzyme include: (X97557; *Saccharomyces cerevisiae*), (AF290095; *Enterococcus faecium*), and (U49260; *Homo sapiens*).

Conversion of IPP to DMAPP

The host cell may contain a heterologous nucleotide sequence encoding an enzyme that can convert IPP generated via the MEV pathway into dimethylallyl pyrophosphate (DMAPP), e.g., an IPP isomerase. Illustrative examples of nucleotide sequences encoding such an enzyme include: (NC_000913, 3031087.3031635; *Escherichia coli*), and (AF082326; *Haematococcus pluvialis*).

Polyprenyl Synthases

In some embodiments, the host cell further comprises a heterologous nucleotide sequence encoding a polyprenyl synthase that can condense IPP and/or DMAPP molecules to form polyprenyl compounds containing more than five carbons.

The host cell may contain a heterologous nucleotide sequence encoding an enzyme that can condense one molecule of IPP with one molecule of DMAPP to form one molecule of geranyl pyrophosphate ("GPP"), e.g., a GPP synthase. Non-limiting examples of nucleotide sequences encoding such an enzyme include: (AF513111; *Abies grandis*), (AF513112; *Abies grandis*), (AF513113; *Abies grandis*), (AY534686; *Antirrhinum majus*), (AY534687; *Antirrhinum majus*), (Y17376; *Arabidopsis thaliana*), (AE016877, Locus AP11092; *Bacillus cereus*; ATCC 14579), (AJ243739; *Citrus sinensis*), (AY534745; *Clarkia brewen*), (AY953508; Ips *pini*), (DQ286930; *Lycopersicon esculentum*), (AF182828; *Mentha xpiperita*), (AF182827; *Mentha×piperita*), (MP1249453; *Mentha×piperita*), (PZE431697, Locus CAD24425; *Paracoccus zeaxanthinifaciens*), (AY866498; *Picrorhiza kurrooa*), (AY351862; *Vitis vinifera*), and (AF203881, Locus AAF12843; *Zymomonas mobilis*).

The host cell may contain a heterologous nucleotide sequence encoding an enzyme that can condense two molecules of IPP with one molecule of DMAPP, or add a molecule of IPP to a molecule of GPP, to form a molecule of farnesyl pyrophosphate ("FPP"), e.g., a FPP synthase. Non-limiting examples of nucleotide sequences that encode a FPP synthase include: (ATU80605; *Arabidopsis thaliana*), (ATHFPS2R; *Arabidopsis thaliana*), (AAU36376; *Artemisia annua*), (AF461050; *Bos taurus*), (D00694; *Escherichia coli* K-12), (AE009951, Locus AAL95523; *Fusobacterium nucleatum* subsp. *nucleatum* ATCC 25586), (GFFPPSGEN; *Gibberella fujikuroi*), (CP000009, Locus AAW60034; *Gluconobacter oxydans* 621H), (AF019892; *Helianthus annuus*), (HUMFAPS; *Homo sapiens*), (KLPFPSQCR; *Kluyveromyces lactis*), (LAU15777; *Lupinus albus*), (LAU20771; *Lupinus albus*), (AF309508; *Mus musculus*), (NCFPPSGEN; *Neurospora crassa*), (PAFPS1; *Parthenium* argentatum), (PAFPS2; *Parthenium* argentatum), (RATFAPS; *Rattus norvegicus*), (YSCFPP; *Saccharomyces cerevisiae*), (D89104; *Schizosaccharomyces pombe*), (CP000003, Locus AAT87386; *Streptococcus pyogenes*), (CP000017, Locus AAZ51849; *Streptococcus pyogenes*), (NC_008022, Locus YP_598856; *Streptococcus pyogenes* MGAS10270), (NC_008023, Locus YP_600845; *Streptococcus pyogenes* MGAS2096), (NC_008024, Locus YP_602832; *Streptococcus pyogenes* MGAS10750), (MZEFPS; *Zea mays*), (AE000657, Locus AAC06913; *Aquifex* aeolicus VF5), (NM_202836; *Arabidopsis thaliana*), (D84432, Locus BAA12575; *Bacillus subtilis*), (U12678, Locus AAC28894; *Bradyrhizobium japonicum* USDA 110), (BACFDPS; *Geobacillus stearothermophilus*), (NC_002940, Locus NP_873754; *Haemophilus ducreyi*35000HP), (L42023, Locus AAC23087; *Haemophilus influenzae* Rd KW20), (J05262; *Homo sapiens*), (YP_395294; *Lactobacillus sakei* subsp. *sakei*23K), (NC_005823, Locus YP_000273; *Leptospira interrogans* serovar Copenhageni str. Fiocruz L1-130), (AB003187; *Micrococcus luteus*), (NC_002946, Locus YP_208768; *Neisseria gonorrhoeae* FA 1090), (U00090, Locus AAB91752; *Rhizobium* sp. NGR234), (J05091; *Saccharomyces cerevisae*), (CP000031, Locus AAV93568; *Silicibacter pomeroyi* DSS-3), (AE008481, Locus AAK99890; *Streptococcus pneumoniae* R6), and (NC_004556, Locus NP 779706; *Xylella fastidiosa* Temecula1).

While examples of the enzymes of the mevalonate pathway are described above, in certain embodiments, enzymes of the DXP pathway can be used as an alternative or additional pathway to produce DMAPP and IPP in the host cells, compositions and methods described herein. Enzymes and nucleic acids encoding the enzymes of the DXP pathway are well-known and characterized in the art, e.g., WO 2012/135591.

Culture Media and Conditions

Materials and methods for the maintenance and growth of microbial cultures are well known to those skilled in the art of microbiology or fermentation science (see, for example, Bailey et al., Biochemical Engineering Fundamentals, second edition, McGraw Hill, New York, 1986). Consideration must be given to appropriate culture medium, pH, temperature, and requirements for aerobic, microaerobic, or anaerobic conditions, depending on the specific requirements of the host cell, the fermentation, and the process.

The methods of producing artemisinic acid provided herein may be performed in a suitable culture medium (e.g., with or without pantothenate supplementation) in a suitable container, including but not limited to a cell culture plate, a microtiter plate, a flask, or a fermentor. Further, the methods can be performed at any scale of fermentation known in the art to support industrial production of microbial products. Any suitable fermentor may be used including a stirred tank fermentor, an airlift fermentor, a bubble fermentor, or any combination thereof. In particular embodiments utilizing *Saccharomyces cerevisiae* as the host cell, strains can be grown in a fermentor as described in detail by Kosaric, et al, in Ullmann's Encyclopedia of Industrial Chemistry, Sixth Edition, vol. 12, pp. 398-473, Wiley-VCH Verlag GmbH & Co. KDaA, Weinheim, Germany.

In some embodiments, the culture medium is any culture medium in which a genetically modified microorganism capable of producing artemisinic acid can subsist. The culture medium may be an aqueous medium comprising assimilable carbon, nitrogen and phosphate sources. Such a medium can also include appropriate salts, minerals, metals, and other nutrients. The carbon source and each of the essential cell nutrients may be added incrementally or continuously to the fermentation media, and each required nutrient may be maintained at essentially the minimum level needed for efficient assimilation by growing cells, for example, in accordance with a predetermined cell growth curve based on the metabolic or respiratory function of the cells which convert the carbon source to a biomass.

Suitable conditions and suitable media for culturing microorganisms are well known in the art. For example, the suitable medium may be supplemented with one or more additional agents, such as, for example, an inducer (e.g., when one or more nucleotide sequences encoding a gene product are under the control of an inducible promoter), a repressor (e.g., when one or more nucleotide sequences encoding a gene product are under the control of a repressible promoter), or a selection agent (e.g., an antibiotic to select for microorganisms comprising the genetic modifications).

The carbon source may be a monosaccharide (simple sugar), a disaccharide, a polysaccharide, a non-fermentable carbon source, or one or more combinations thereof. Non-limiting examples of suitable monosaccharides include glucose, galactose, mannose, fructose, xylose, ribose, and combinations thereof. Non-limiting examples of suitable disaccharides include sucrose, lactose, maltose, trehalose, cellobiose, and combinations thereof. Non-limiting examples of suitable polysaccharides include starch, glycogen, cellulose, chitin, and combinations thereof. Non-limiting examples of suitable non-fermentable carbon sources include acetate and glycerol.

The concentration of a carbon source, such as glucose, in the culture medium may be sufficient to promote cell growth but is not so high as to repress growth of the microorganism used. Typically, cultures are run with a carbon source, such as glucose, being added at levels to achieve the desired level of growth and biomass. The concentration of a carbon source, such as glucose, in the culture medium may be greater than about 1 g/L, preferably greater than about 2 g/L, and more preferably greater than about 5 g/L. In addition, the concentration of a carbon source, such as glucose, in the culture medium is typically less than about 100 g/L, preferably less than about 50 g/L, and more preferably less than about 20 g/L. It should be noted that references to culture component concentrations can refer to both initial and/or ongoing component concentrations. In some cases, it may be desirable to allow the culture medium to become depleted of a carbon source during culture.

Sources of assimilable nitrogen that can be used in a suitable culture medium include simple nitrogen sources, organic nitrogen sources and complex nitrogen sources. Such nitrogen sources include anhydrous ammonia, ammonium salts and substances of animal, vegetable and/or microbial origin.

Suitable nitrogen sources include protein hydrolysates, microbial biomass hydrolysates, peptone, yeast extract, ammonium sulfate, urea, and amino acids. Typically, the concentration of the nitrogen sources, in the culture medium is greater than about 0.1 g/L, preferably greater than about 0.25 g/L, and more preferably greater than about 1.0 g/L. Beyond certain concentrations, however, the addition of a nitrogen source to the culture medium is not advantageous for the growth of the microorganisms. As a result, the concentration of the nitrogen sources, in the culture medium is less than about 20 g/L, preferably less than about 10 g/L and more preferably less than about 5 g/L. Further, in some instances it may be desirable to allow the culture medium to become depleted of the nitrogen sources during culture.

The effective culture medium may contain other compounds such as inorganic salts, vitamins, trace metals or growth promoters. Such other compounds may also be present in carbon, nitrogen or mineral sources in the effective medium or can be added specifically to the medium.

The culture medium may also contain a suitable phosphate source. Such phosphate sources include both inorganic and organic phosphate sources. Preferred phosphate sources include phosphate salts such as mono or dibasic sodium and potassium phosphates, ammonium phosphate and mixtures thereof. Typically, the concentration of phosphate in the culture medium is greater than about 1.0 g/L, preferably greater than about 2.0 g/L and more preferably greater than about 5.0 g/L. Beyond certain concentrations, however, the addition of phosphate to the culture medium is not advantageous for the growth of the microorganisms. Accordingly, the concentration of phosphate in the culture medium is typically less than about 20 g/L, preferably less than about 15 g/L and more preferably less than about 10 g/L.

A suitable culture medium can also include a source of magnesium, preferably in the form of a physiologically acceptable salt, such as magnesium sulfate heptahydrate, although other magnesium sources in concentrations that contribute similar amounts of magnesium can be used. Typically, the concentration of magnesium in the culture medium is greater than about 0.5 g/L, preferably greater than about 1.0 g/L, and more preferably greater than about 2.0 g/L. Beyond certain concentrations, however, the addition of magnesium to the culture medium is not advantageous for the growth of the microorganisms. Accordingly, the concentration of magnesium in the culture medium is typically less than about 10 g/L, preferably less than about 5 g/L, and more preferably less than about 3 g/L. Further, in some instances it may be desirable to allow the culture medium to become depleted of a magnesium source during culture.

The culture medium can also include a biologically acceptable chelating agent, such as the dihydrate of trisodium citrate. In such instance, the concentration of a chelating agent in the culture medium is greater than about 0.2 g/L, preferably greater than about 0.5 g/L, and more preferably greater than about 1 g/L. Beyond certain concentrations, however, the addition of a chelating agent to the culture medium is not advantageous for the growth of the microorganisms. Accordingly, the concentration of a chelating agent in the culture medium is typically less than about 10 g/L, preferably less than about 5 g/L, and more preferably less than about 2 g/L.

The culture medium may also initially include a biologically acceptable acid or base to maintain the desired pH of the culture medium. Biologically acceptable acids include, but are not limited to, hydrochloric acid, sulfuric acid, nitric acid, phosphoric acid and mixtures thereof. Biologically acceptable bases include, but are not limited to, ammonium hydroxide, sodium hydroxide, potassium hydroxide and mixtures thereof. In some embodiments, the base used is ammonium hydroxide.

The culture medium may also include a biologically acceptable calcium source, including, but not limited to, calcium chloride. Typically, the concentration of the calcium source, such as calcium chloride, dihydrate, in the culture medium is within the range of from about 5 mg/L to about 2000 mg/L, preferably within the range of from about 20 mg/L to about 1000 mg/L, and more preferably in the range of from about 50 mg/L to about 500 mg/L.

The culture medium may also include sodium chloride. Typically, the concentration of sodium chloride in the culture medium is within the range of from about 0.1 g/L to about 5 g/L, preferably within the range of from about 1 g/L to about 4 g/L, and more preferably in the range of from about 2 g/L to about 4 g/L.

The culture medium may also include trace metals. Such trace metals can be added to the culture medium as a stock solution that, for convenience, can be prepared separately from the rest of the culture medium. Typically, the amount of such a trace metals solution added to the culture medium is greater than about 1 ml/L, preferably greater than about 5 mL/L, and more preferably greater than about 10 mL/L. Beyond certain concentrations, however, the addition of a trace metals to the culture medium is not advantageous for the growth of the microorganisms. Accordingly, the amount of such a trace metals solution added to the culture medium is typically less than about 100 mL/L, preferably less than about 50 mL/L, and more preferably less than about 30 mL/L. It should be noted that, in addition to adding trace metals in a stock solution, the individual components can be added separately, each within ranges corresponding independently to the amounts of the components dictated by the above ranges of the trace metals solution.

The culture media may include other vitamins, such as pantothenate, biotin, calcium, pantothenate, inositol, pyridoxine-HCl, and thiamine-HCl. Such vitamins can be added to the culture medium as a stock solution that, for convenience, can be prepared separately from the rest of the culture medium. Beyond certain concentrations, however, the addition of vitamins to the culture medium is not advantageous for the growth of the microorganisms.

The fermentation methods described herein can be performed in conventional culture modes, which include, but are not limited to, batch, fed-batch, cell recycle, continuous and semi-continuous. In some embodiments, the fermentation is carried out in fed-batch mode. In such a case, some of the components of the medium are depleted during culture, including pantothenate during the production stage of the fermentation. In some embodiments, the culture may be supplemented with relatively high concentrations of such components at the outset, for example, of the production stage, so that growth and/or artemisinic acid production is supported for a period of time before additions are required. The preferred ranges of these components are maintained throughout the culture by making additions as levels are depleted by culture. Levels of components in the culture medium can be monitored by, for example, sampling the culture medium periodically and assaying for concentrations. Alternatively, once a standard culture procedure is developed, additions can be made at timed intervals corresponding to known levels at particular times throughout the culture. As will be recognized by those in the art, the rate of consumption of nutrient increases during culture as the cell density of the medium increases. Moreover, to avoid introduction of foreign microorganisms into the culture medium, addition is performed using aseptic addition methods, as are known in the art. In addition, an anti-foaming agent may be added during the culture.

The temperature of the culture medium can be any temperature suitable for growth of the genetically modified cells and/or production of artemisinic acid. For example, prior to inoculation of the culture medium with an inoculum, the culture medium can be brought to and maintained at a temperature in the range of from about 20° C. to about 45° C., preferably to a temperature in the range of from about 25° C. to about 40° C., and more preferably in the range of from about 28° C. to about 32° C. The pH of the culture medium can be controlled by the addition of acid or base to the culture medium. In such cases when ammonium hydroxide is used to control pH, it also conveniently serves as a nitrogen source in the culture medium. Preferably, the pH is maintained from about 3.0 to about 8.0, more preferably from about 3.5 to about 7.0, and most preferably from about 4.0 to about 6.5.

The carbon source concentration, such as the glucose concentration, of the culture medium is monitored during culture. Glucose concentration of the culture medium can be monitored using known techniques, such as, for example, use of the glucose oxidase enzyme test or high pressure liquid chromatography, which can be used to monitor glucose concentration in the supernatant, e.g., a cell-free component of the culture medium. The carbon source concentration is typically maintained below the level at which cell growth inhibition occurs. Although such concentration may vary from organism to organism, for glucose as a carbon source, cell growth inhibition occurs at glucose concentrations greater than at about 60 g/L, and can be determined readily by trial. Accordingly, when glucose is used as a carbon source the glucose is preferably fed to the fermentor and maintained below detection limits. Alternatively, the glucose concentration in the culture medium is maintained in the range of from about 1 g/L to about 100 g/L, more preferably in the range of from about 2 g/L to about 50 g/L, and yet more preferably in the range of from about 5 g/L to about 20 g/L. Although the carbon source concentration can be maintained within desired levels by addition of, for example, a substantially pure glucose solution, it is acceptable, and may be preferred, to maintain the carbon source concentration of the culture medium by addition of aliquots of the original culture medium. The use of aliquots of the original culture medium may be desirable because the concentrations of other nutrients in the medium (e.g. the nitrogen and phosphate sources) can be maintained simultaneously. Likewise, the trace metals concentrations can be maintained in the culture medium by addition of aliquots of the trace metals solution.

Other suitable fermentation medium and methods are described in, e.g., WO 2016/196321.

Methods of Making Genetically Modified Cells

Also provided herein are methods for producing a host cell that is genetically engineered to contain one or more of the modifications described above, e.g., one or more heterologous nucleic acids encoding *Amorpha*-4,11-diene 12-monooxygenase, and/or biosynthetic pathway enzymes, e.g., for artemisinic acid. Expression of a heterologous enzyme in a host cell can be accomplished by introducing into the host cells a nucleic acid comprising a nucleotide sequence encoding the enzyme under the control of regulatory elements that permit expression in the host cell. The nucleic acid may be an extrachromosomal plasmid, a chromosomal integration vector that can integrate the nucleotide sequence into the chromosome of the host cell, or a linear piece of double stranded DNA that can integrate via homology the nucleotide sequence into the chromosome of the host cell.

Nucleic acids encoding these proteins can be introduced into the host cell by any method known to one of skill in the art (see, e.g., Hinnen et al., (1978) *Proc. Natl. Acad. Sci. USA*, vol. 75, pp. 1292-1293; Cregg et al., (1985), *Mol. Cell. Biol.*, vol. 5, pp. 3376-3385; Goeddel et al. eds, 1990, *Methods in Enzymology*, vol. 185, Academic Press, Inc., CA; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY). Exemplary techniques include, spheroplasting, electroporation, PEG 1000 mediated transformation, and lithium acetate or lithium chloride mediated transformation.

The amount of an enzyme in a host cell may be altered by modifying the transcription of the gene that encodes the enzyme. This can be achieved by modifying the copy number of the nucleotide sequence encoding the enzyme (e.g., by using a higher or lower copy number expression vector comprising the nucleotide sequence, or by introducing additional copies of the nucleotide sequence into the genome of the host cell or by deleting or disrupting the nucleotide sequence in the genome of the host cell), by changing the order of coding sequences on a polycistronic mRNA of an operon or breaking up an operon into individual genes each with its own control elements, or by increasing the strength of the promoter or operator to which the nucleotide sequence is operably linked. Alternatively, or in addition, the copy number of an enzyme in a host cell may be altered by modifying the level of translation of an mRNA that encodes the enzyme. This can be achieved by modifying the stability of the mRNA, modifying the sequence of the ribosome binding site, modifying the distance or sequence between the ribosome binding site and the start codon of the enzyme coding sequence, modifying the entire intercistronic region located "upstream of" or adjacent to the 5' side of the start codon of the enzyme coding region, stabilizing the 3'-end of the mRNA transcript using hairpins and specialized sequences, modifying the codon usage of enzyme, altering expression of rare codon tRNAs used in the biosynthesis of the enzyme, and/or increasing the stability of the enzyme, as, for example, via mutation of its coding sequence.

The activity of an enzyme in a host cell may be altered in a number of ways, including expressing a modified form of the enzyme that exhibits increased or decreased solubility in the host cell, expressing an altered form of the enzyme that lacks a domain through which the activity of the enzyme is inhibited, expressing a modified form of the enzyme that has a higher or lower $K_{cat}$ or a lower or higher $K_m$ for the substrate, expressing a modified form of the enzyme that has a higher or lower thermostability, expressing a modified form of the enzyme that has a higher or lower activity at the pH of the cell, expressing a modified form of the enzyme that has a higher or lower accumulation in a subcellular compartment or organelle, expressing a modified form of the enzyme that has increased or decreased ability to insert into or associate with cellular membranes, expressing a modified form of the enzyme that has a higher or lower affinity for accessory proteins needed to carry out a reaction, expressing a modified form of the enzyme that has a higher or lower affinity for necessary cofactors or ligands, expressing a modified form of the enzyme that has an increased or decreased space in the active site (thereby differentially allowing or excluding different substrates for the reaction), or expressing an altered form of the enzyme that is more or less affected by feed-back or feed-forward regulation by another molecule in the pathway.

A nucleic acid used to genetically modify a host cell may contain one or more selectable markers useful for the selection of transformed host cells and for placing selective pressure on the host cell to maintain the foreign DNA.

The selectable marker may be an antibiotic resistance marker. Examples of antibiotic resistance markers include the BLA, NAT1, PAT, AUR1-C, PDR4, SMR1, CAT, mouse dhfr, HPH, DSDA, $KAN^R$, and SH BLE gene products. The BLA gene product from *E. coli* confers resistance to beta-lactam antibiotics (e.g., narrow-spectrum cephalosporins, cephamycins, and carbapenems (ertapenem), cefamandole, and cefoperazone) and to all the anti-gram-negative-bacterium penicillins except temocillin; the NAT1 gene product from *S. noursei* confers resistance to nourseothricin; the PAT gene product from *S. viridochromogenes* Tu94 confers resistance to bialophos; the AUR1-Cgene product from *Saccharomyces cerevisiae* confers resistance to Auerobasidin A (AbA); the PDR4 gene product confers resistance to cerulenin; the SMR1 gene product confers resistance to sulfometuron methyl; the CAT gene product from Tn9 transposon confers resistance to chloramphenicol; the mouse dhfr gene product confers resistance to methotrexate; the HPH gene product of *Klebsiella pneumonia* confers resistance to Hygromycin B; the DSDA gene product of *E. coli* allows cells to grow on plates with D-serine as the sole nitrogen source; the $KAN^R$ gene of the Tn903 transposon confers resistance to G418; and the SH BLE gene product from *Streptoalloteichus hindustanus* confers resistance to Zeocin (bleomycin). The antibiotic resistance marker may be deleted after the genetically modified host cell disclosed herein is isolated.

The selectable marker may function by rescue of an auxotrophy (e.g., a nutritional auxotrophy) in the genetically modified microorganism. In auxotrophy, a parent microorganism contains a functional disruption in one or more gene products that function in an amino acid or nucleotide biosynthetic pathway and that renders the parent cell incapable of growing in media without supplementation with one or more nutrients. Such gene products include the HIS3, LEU2, LYS1, LYS2, MET15, TRP1, ADE2, and URA3 gene products in yeast. The auxotrophic phenotype can then be rescued by transforming the parent cell with an expression vector or chromosomal integration construct encoding a functional copy of the disrupted gene product, and the genetically modified host cell generated can be selected for based on the loss of the auxotrophic phenotype of the parent cell. Utilization of the URA3, TRP1, and LYS2 genes as selectable markers has a marked advantage because both positive and negative selections are possible. Positive selection is carried out by auxotrophic complementation of the URA3, TRP1, and LYS2 mutations, whereas negative selection is based on specific inhibitors, i.e., 5-fluoro-orotic acid (FOA), 5-fluoroanthranilic acid, and aminoadipic acid (aAA), respectively, that prevent growth of the prototrophic strains but allows growth of the URA3, TRP1, and LYS2 mutants, respectively. The selectable marker may rescue other non-lethal deficiencies or phenotypes that can be identified by a known selection method.

Described herein are specific genes and proteins useful in the methods, compositions, and host cells of the invention; however, the absolute identity to such genes is not necessary. For example, changes in a particular gene or polynucleotide containing a sequence encoding a polypeptide or enzyme can be performed and screened for activity. Typically, such changes involve conservative mutations and silent mutations. Such modified or mutated polynucleotides and polypeptides can be screened for expression of a functional enzyme using methods known in the art.

Due to the inherent degeneracy of the genetic code, other polynucleotides which encode substantially the same or functionally equivalent polypeptides may also be used to express the enzymes.

It can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, in a process sometimes called "codon optimization" or "controlling for species codon bias." Codon optimization for other host cells can be readily determined using codon usage tables or can be performed using commercially available software, such as CodonOp from Integrated DNA Technologies.

Optimized coding sequences containing codons preferred by a particular prokaryotic or eukaryotic host (Murray et al., (1989), *Nucl Acids Res*., vol. 17, pp. 477-508) can be prepared, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al., (1996), *Nucl Acids Res*., vol. 24, pp. 216-218).

Due to the degenerate nature of the genetic code, a variety of DNA molecules differing in their nucleotide sequences may be used to encode a given enzyme of the disclosure. The native DNA sequence encoding the biosynthetic enzymes described above are referenced herein merely to illustrate an embodiment of the disclosure, and the disclosure includes DNA molecules of any sequence that encode the amino acid sequences of the polypeptides and proteins of the enzymes utilized in the methods of the invention. In similar fashion, a polypeptide can typically tolerate one or more amino acid substitutions, deletions, and insertions in its amino acid sequence without loss or significant loss of a desired activity. The invention includes such polypeptides with different amino acid sequences than the specific proteins described herein so long as the modified or variant polypeptides have the enzymatic activity of the reference polypeptide. Furthermore, the amino acid sequences encoded by the DNA sequences shown herein merely illustrate examples of the invention.

In addition, homologs of enzymes useful for the practice of the compositions, methods, or host cells are encompassed by the invention. Two proteins (or a region of the proteins) are considered to be substantially homologous when the amino acid sequences have at least about 30%, 40%, 50%, 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes may be at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (See, e.g., Pearson W. R., (1994), *Methods in Mol Biol*, vol. 25, pp. 365-389).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. A typical algorithm used for comparing a molecule sequence to a database containing a large number of sequences from different organisms is the computer program BLAST. When searching a database containing sequences from a large number of different organisms, it is typical to compare amino acid sequences.

Furthermore, any of the genes encoding the foregoing enzymes or any of the regulatory elements that control or modulate their expression may be optimized by genetic/protein engineering techniques, such as directed evolution or rational mutagenesis. Such action allows those of ordinary skill in the art to optimize the enzymes for expression and activity in yeast.

In addition, genes encoding these enzymes can be identified from other fungal and bacterial species and can be expressed for the modulation of the artemisinic acid pathway. A variety of organisms may serve as sources for these enzymes, including *Saccharomyces* spp., including *S. cerevisiae* and *S. uvarum, Kluyveromyces* spp., including *K. thermotolerans, K. lactis*, and *K. marxianus, Pichia* spp., *Hansenula* spp., including *H. polymorpha, Candida* spp., *Trichosporon* spp., *Yamadazyma* spp., including Y. spp. *stipitis, Torulaspora pretoriensis, Issatchenkia orientalis, Schizosaccharomyces* spp., including *S. pombe, Cryptococcus* spp., *Aspergillus* spp., *Neurospora* spp., or *Ustilago* spp. Sources of genes from anaerobic fungi include *Piromyces* spp., *Orpinomyces* spp., or *Neocallimastix* spp. Sources of prokaryotic enzymes that are useful include *Escherichia. coli, Zymomonas mobilis, Staphylococcus aureus, Bacillus* spp., *Clostridium* spp., *Corynebacterium* spp., *Pseudomonas* spp., *Lactococcus* spp., *Enterobacter* spp., and *Salmonella* spp.

Techniques known to those skilled in the art may be suitable to identify additional homologous genes and enzymes. Generally, analogous genes and/or analogous enzymes can be identified by functional analysis and will have functional similarities. Techniques known to be suitable to identify analogous genes and analogous enzymes include PCR, degenerate PCR, low stringency nucleic acid hybridization, expression cloning, and high through-put screening. For example, to identify homologous or analogous *Amorpha*-4,11-diene 12-monooxygenase, alcohol dehydrogenase, aldehyde dehydrogenase, or any artemisinic acid biosynthetic pathway genes, proteins, or enzymes, techniques may include, but are not limited to, cloning a gene by PCR using primers based on a published sequence of a gene/enzyme of interest, or by degenerate PCR using degenerate primers designed to amplify a conserved region among a gene of interest. Further, one may use techniques to identify homologous or analogous genes, proteins, or enzymes with functional homology or similarity. Techniques include examining a cell or cell culture for the catalytic activity of an enzyme through in vitro enzyme assays for said activity (e.g. as described herein or in Kiritani, K., *Branched-Chain Amino Acids Methods Enzymology,* 1970), then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or similar genes and/or homologous or similar enzymes, analogous genes and/or analogous enzymes or proteins, techniques also include comparison of data concerning a candidate gene or enzyme with databases such as BRENDA, KEGG, or MetaCYC. The candidate gene or enzyme may be identified within the above-mentioned databases in accordance with the teachings herein.

EXAMPLES

Example 1: p450 Variant Screening Strains

An artemisinic acid-producing yeast strain, strain Y26454, expresses the wild-type version of CYP71AV1 (the gene encoding *Artemisia annua amorpha*-4,11-diene 12-monooxygenase). A number of lines of evidence indicated that during production-scale fermentation of artemisinic acid, the activity of *Amorpha*-4,11-diene 12-monooxygenase was a rate limiting bottleneck, with only about 60% of the precursor amorphadiene being converted to artemisinic acid. However, attempts to improve the strain by screening for variants of the enzyme with increased activity failed because, when Y26454 was cultured in the typical 96 well plate-based assay format, nearly all of amorphadiene was converted to artemisinic acid. The difference in Y26454 performance between plate and tank fermentation is shown in FIG. 1. This near complete reaction did not provide enough headroom to identify any variants with increased activity compared to the wild-type enzyme.

Figure 2:
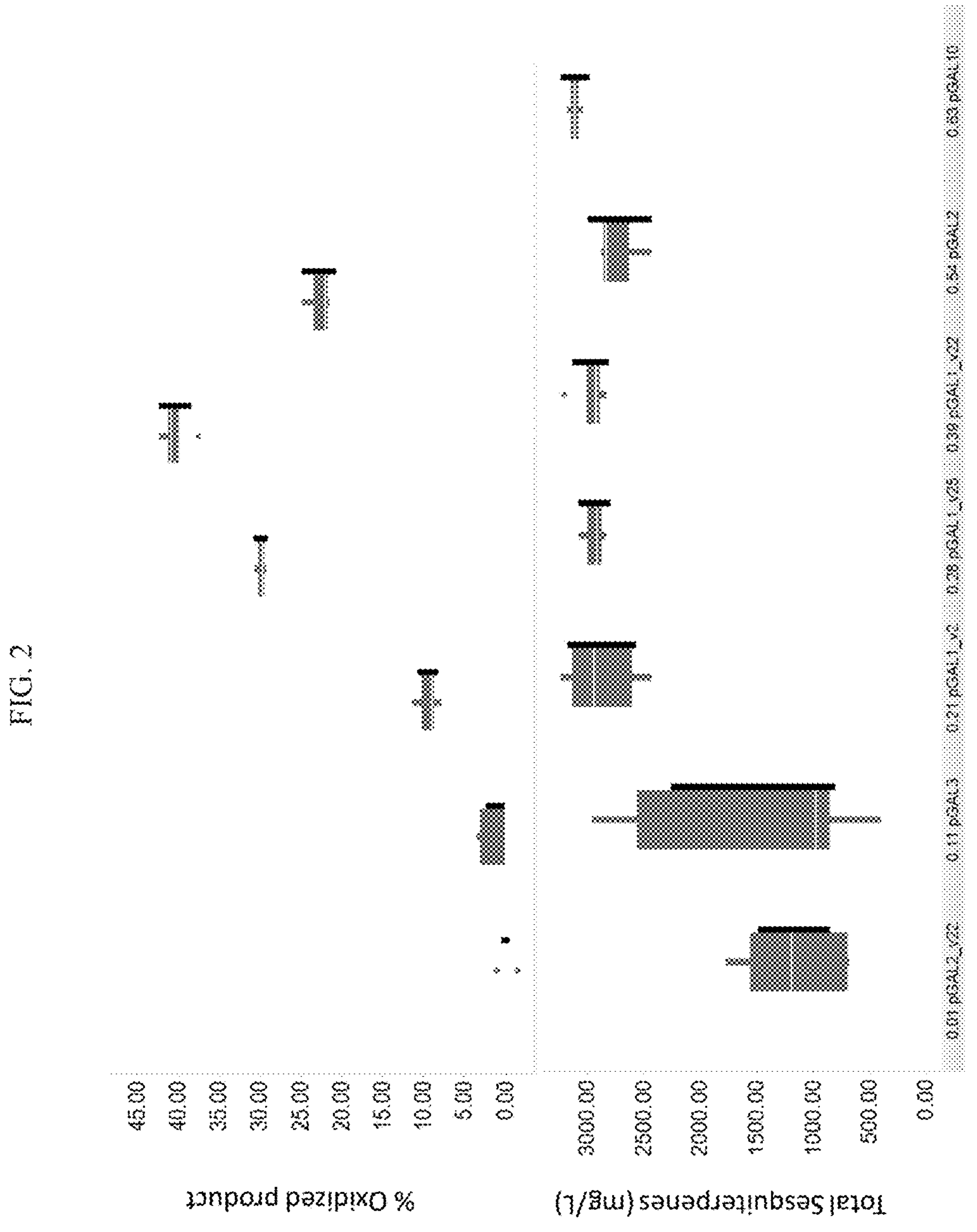
FIG. 2 is a set of graphs showing the amount of oxidized product and total sesquiterpene production in various potential screening strains that have placed the *Amorpha*-4,11-diene 12-monooxygenase coding sequence under control of various weak promoters.

To overcome the barrier to 96 well plate-based screening, strains were developed that provided for reduced expression of the CYP71AV1 gene, the notion being that expressing suboptimal levels of the enzyme would lower the threshold floor of activity upon which even slight to moderate activity increases could be measured. An optimal screening strain would be one that demonstrated decreased oxidation of amorphadiene but which maintained relatively high total sesquiterpene levels. Strains with these qualities were identified by placing the CYP71AV1 gene under control of a panel of promoters and testing each strain for reduced oxidation of amorphadiene but relatively high sesquiterpene levels (see FIG. 2).

Figure 3:
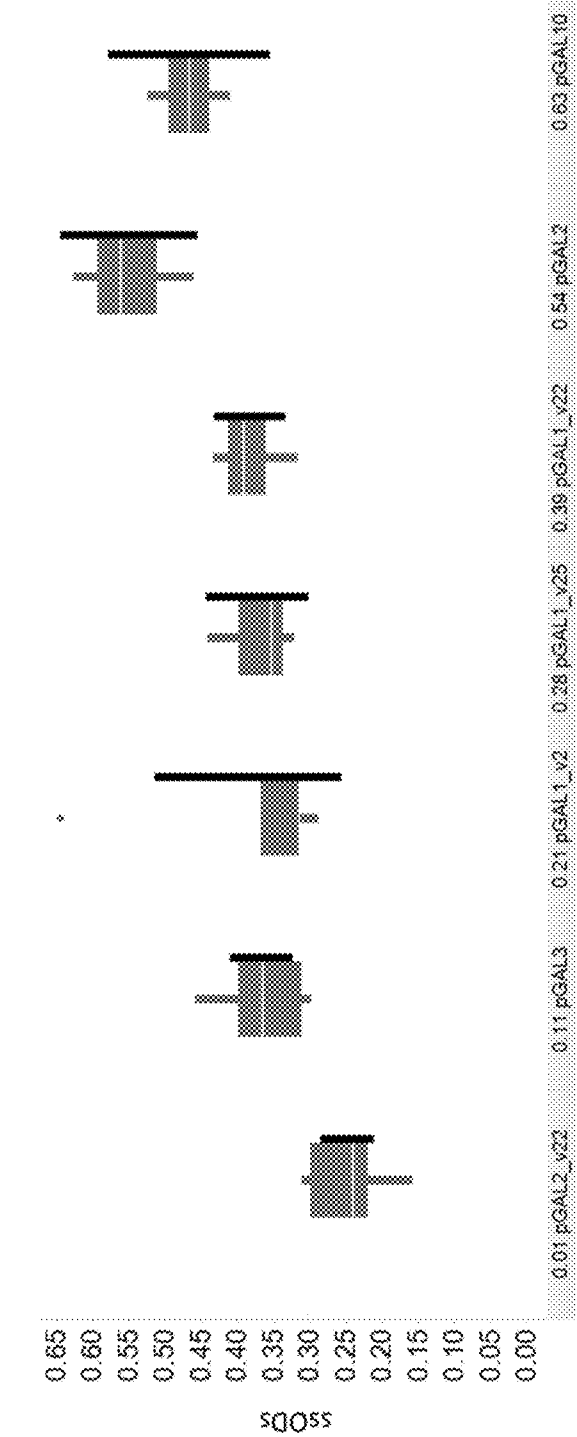
FIG. 3 is a graph showing the growth (ssODs) of different strains expressing wild-type *Amorpha*-4,11-diene 12-monooxygenase coding sequence under control of various weak promoters.

Growth of these strains was measured using ssOD, which measures the OD of cells in a diluent that reduces optical interference from the presence of sesquiterpenes (See FIG. 3).

Example 2: Yeast Transformation Methods

Each DNA construct was integrated into *Saccharomyces cerevisiae* (CEN.PK113-7D) using standard molecular biology techniques in an optimized lithium acetate (LiAc) transformation. Briefly, cells were grown overnight in yeast extract peptone dextrose (YPD) with 1% maltose and 2 g/L lysine media at 30° C. with shaking (200 rpm), diluted to an $OD_{600}$ of 0.1 in 100 mL YPD with 1% maltose and 2 g/L lysine, and grown to an $OD_{600}$ of 0.6-0.8. For each transformation, 5 mL of culture was harvested by centrifugation, washed in 5 mL of sterile water, spun down again, resuspended in 1 mL of 100 mM LiAc, and transferred to a microcentrifuge tube. Cells were spun down (13,000×g) for 30 seconds, the supernatant was removed, and the cells were resuspended in a transformation mix consisting of 240 μL 50% PEG, 36 μL 1 M LiAc, 10 μL boiled salmon sperm DNA, and 74 μL of donor DNA. For transformations that required expression of the endonuclease F-Cph1, the donor DNA included a plasmid carrying the F-Cph1 gene expressed under the yeast TDH3 promoter for expression. This will cut the F-Cph1 endonuclease recognition site in the landing pad to facilitate integration of the target gene of interest. Following a heat shock at 42° C. for 40 minutes, cells were recovered overnight in YPD media before plating on selective media. DNA integration was confirmed by colony PCR with primers specific to the integrations.

Example 3: Evolution of *Amorpha*-4,11-Diene 12-Monooxygenase via Site Directed Saturation Mutagenesis In this example, activity data is provided for wild type *Amorpha*-4,11-diene 12-monooxygenase and specific mutations that improve *Amorpha*-4,11-diene 12-monooxygenase activity expressed in *S. cerevisiae* in vivo to produce artemisinic acid.

Each amino acid residue in *Amorpha*-4,11-diene 12-monooxygenase was mutated by ordering a single site saturation library from Twist Bioscience (San Francisco, CA). A library of the entire *Amorpha*-4,11-diene 12-monooxygenase coding sequence, along with 150 bp of flanking homology on either end for cloning purposes, was synthesized so that every amino acid position excluding the start codon contained each possible amino acid (wild type amino acid plus 19 non-wild type variants), with one mutation per molecule. Overall, the library contained 9762 variants of a possible 9880 (494 positions×20 possible amino acids per position), with 477 positions containing all 20 possible variants. Only 3 positions had more than 2 substitutions fail synthesis (constructs either violated design constraints, e.g. by introducing restriction sites, or were not detected during QC). The 20 variants at each amino acid position were pooled together, and the library for each position was individually transformed into our screening strain using the 150 bp of flanking homology to direct integration, resulting in the mutant *Amorpha*-4,11-diene 12-monooxygenase being expressed under the relatively weak pGAL2 promoter. Forty individual colonies were picked from each transformation for screening for artemisinic acid production in 96-well plates for 2× coverage of the mutations.

Figure 4:
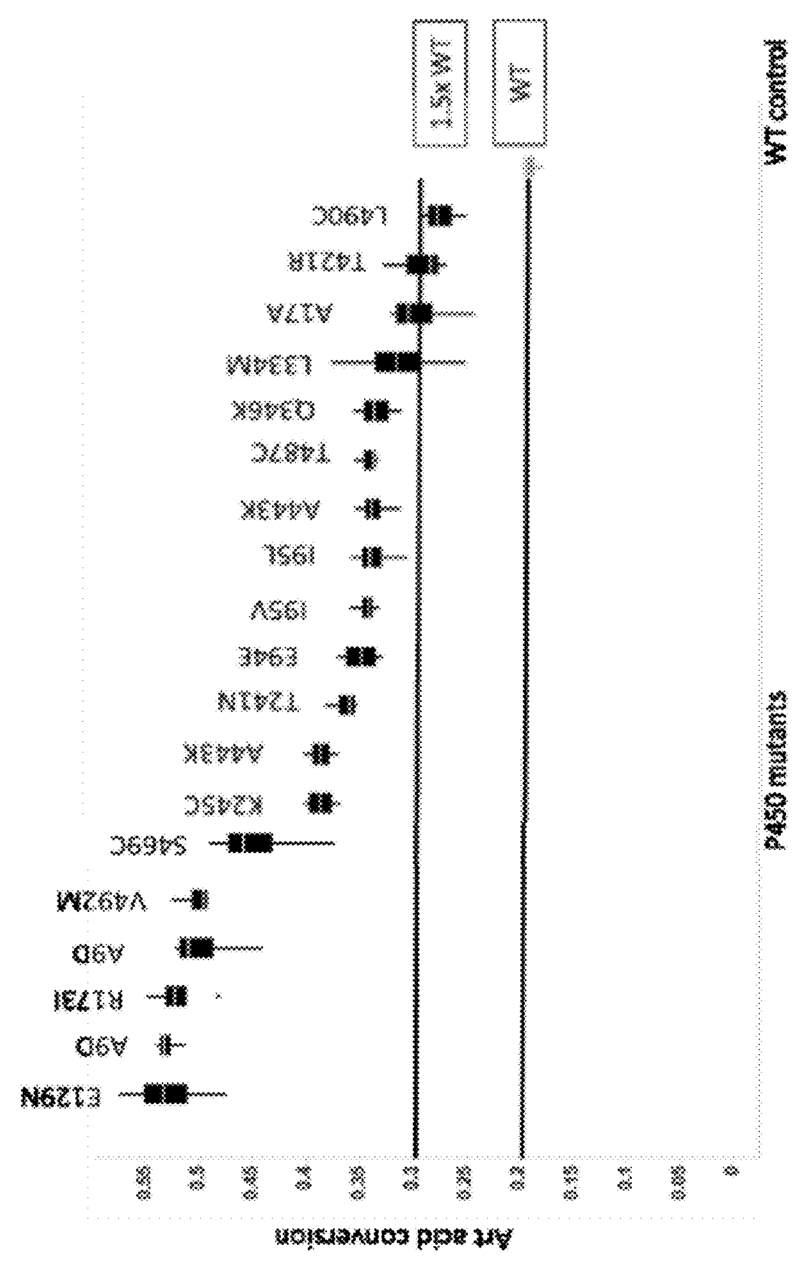
FIG. 4 is a graph showing the activity of the top first tier enzyme variants compared to the activity of the wild-type parent enzyme when expressed under a weak promoter. Activity is shown by production of artemisinic acid as a proportion of total sesquiterpenes in strains expressing single-site mutations in CYP71AV1 relative to wild-type CYP71AV1.

The initial screening identified the following amino acid substitutions that resulted in variant enzymes with increased activity relative to parent wild-type enzyme: A8D, 194L, 194V, E128N, R172I, T240N, K244C, L333M, Q345K, T420R, A442K, A442S, Q449K, S468C, T486C, L489C, and V491 M (See FIG. 4). A subset of 10 of these top variants (A8D, 194V, E128N, V219I, T240N, L333M, L350F, T420R, A442K, and Q449K) was chosen to generate our combinatorial library, spacing the mutations out across the entire sequence. The library was generated by breaking the entire amino acid sequence into 3 fragments for synthesis. Fragment 1 spanned mutations A8D, 194V, and E128N;

fragment 2 contained V219I, T240N, and L333M; fragment 3 contained L350F, T420R, A442K, and Q449K. All 8 possible combinations of fragments 1 and 2 were ordered (all possible combinations of wild type or mutated amino acids for each of 3 positions), and 16 combinations for fragment 3. The fragments contain regions of homology with neighboring fragments. All 32 gene fragments were pooled together and assembled into full-length P450 sequences through overlap extension (OE) PCR. Samples from the OE-PCR reaction were sent for sequence analysis to confirm the presence of wild type and mutant variants for all positions.

The combinatorial library of amino acid variants was then transformed into the low P450 expression screening strain. Screening identified combinatorial variants that had heightened activity relative to parental wild-type and the first round of variants in our low-promoter strength strain, and comparable titers to wild type in a production strain (see Table 2). In particular, the following combinations of amino acid substitutions were found to be beneficial to enzyme activity enhancement: A8D, 194V, E128N, V219I, T240N, L350F, and Q449K; A8D, 194V, E128N, V219I, T240N, L333M, L350F, and Q449K; A8D, E128N, V219I, L350I, and Q449K; and A8D, E128N, V219I, L350F, and Q449K.

Example 4: Improved Single Mutant Variants

Improved single mutant variants of *Amorpha*-4,11-Diene 12-Monooxygenase were identified by improved production of artemisinic acid when expressed from a weak promoter in 96-well plates with hydrophobic overlay outperform the wild type P450 in plates containing overlay.

Figure 5:
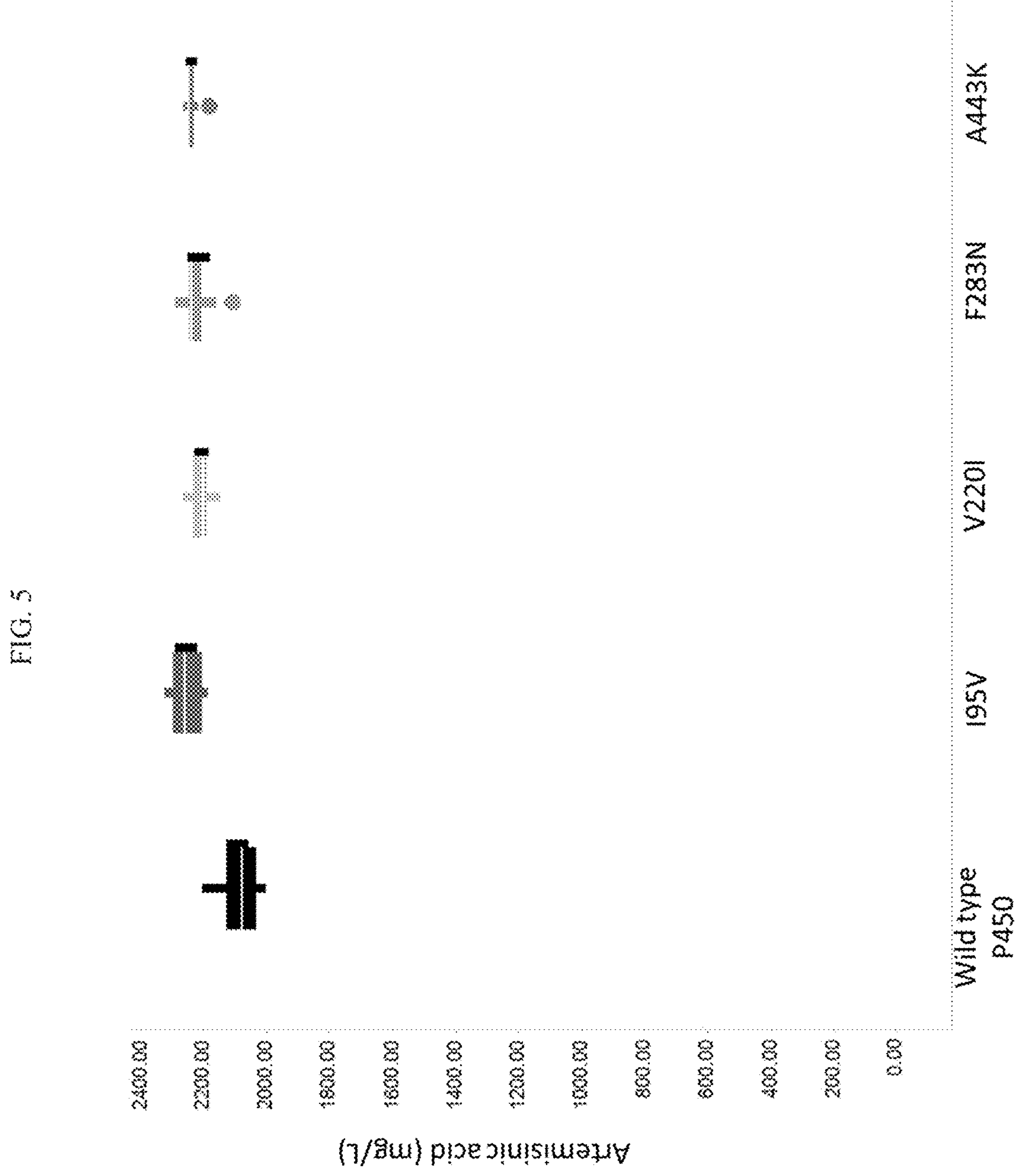
FIG. 5 shows artemisinic acid titers of strains expressing the top single amino acid variants or wild-type P450 under control of high-expression promoters grown in microtiter plates.

A subset of the *Amorpha*-4,11-Diene 12-Monooxygenase mutants with the amino acid substitutions identified in Example 3 (see FIG. 4) were transformed into a host strain with higher P450 expression levels and artemisinic acid production was measured in 96-well plates with hydrophobic overlay. Several of these mutants led to significantly higher art acid titers when compared to an isogenic strain expressing the wild type P450, including 194V, V219I, F237N, and A442K (FIG. 5).

Example 5: Improved Combinatorial Variants

Combinatorial mutant variants of *Amorpha*-4,11-Diene 12-Monooxygenase were identified by improved production of artemisinic acid when expressed from a weak promoter in 96-well plates with hydrophobic overlay produce similar AA titers compared to the wild-type P450 when expressed from strong promoters in a production strain background.

Figure 6:
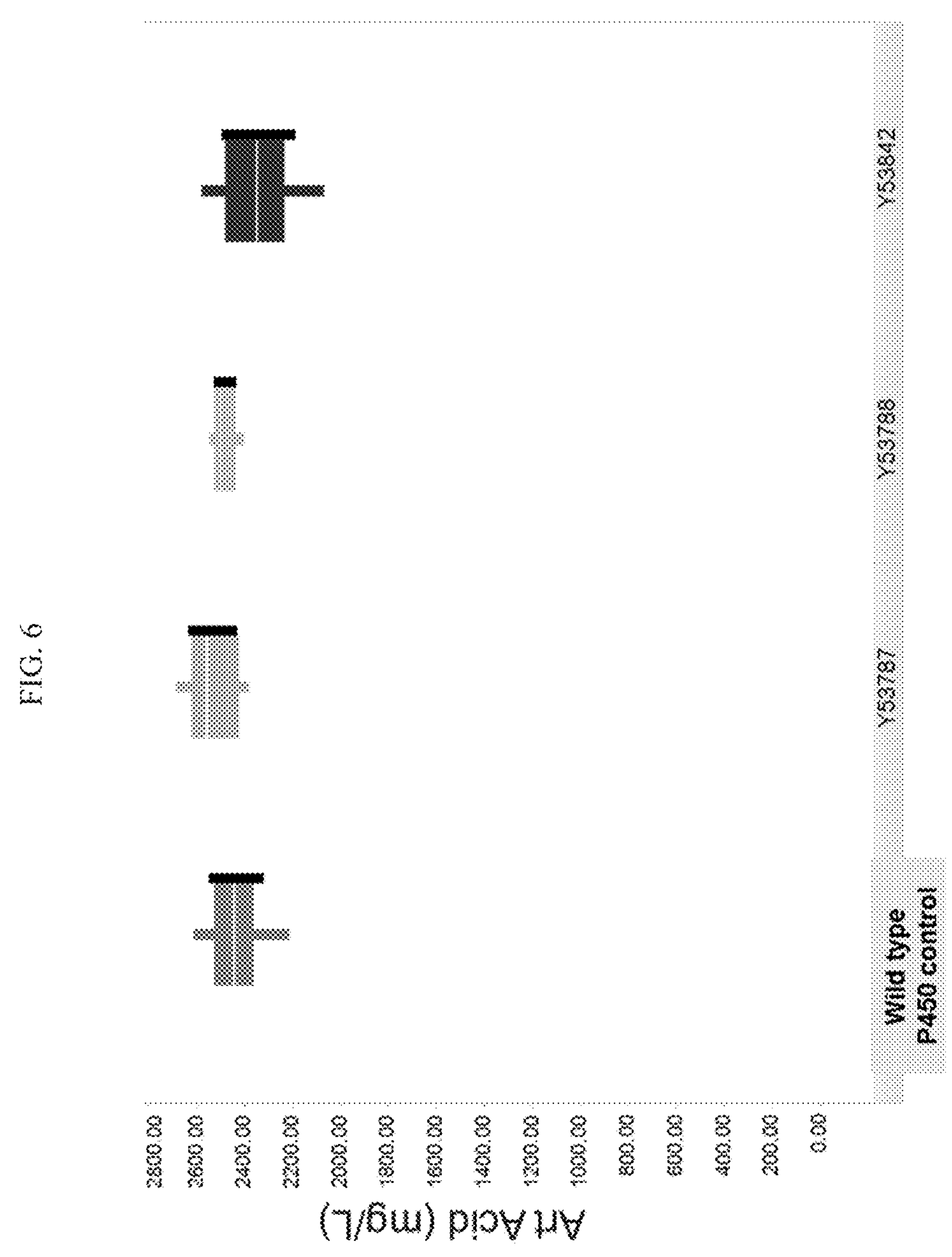
FIG. 6 is a graph showing artemisinic acid production by strains expressing the wild type P450 or top combinatorial library mutant variants identified from our low-expression screening strain in a high-expression production strain background. Growth was in wells in a 96-well plate containing hydrophobic overlay.

Screening of our combinatorial mutant variants of *Amorpha*-4,11-Diene 12-Monooxygenase in our weak-promoter screening strain identified several combinations of amino acid variants that increased artemisinic acid production relative to the wild type strain by over 2-fold. These mutant P450s were ported to a production strain with high-expression promoters driving the P450. Artemisinic acid titers were then measured in 96-well plates for strains grown with hydrophobic overlay. Data for a subset of these strains is shown in FIG. 6. Artemisinic acid titers for the combinatorial mutant strains were statistically indistinguishable from an isogenic strain with the wild type P450. This, highlights the need to screen for improved *Amorpha*-4,11-Diene 12-Monooxygenase variants in a low-expression strain.

Example 6: Variant Characterization

Improved single and multiple amino acid variants of *Amorpha*-4,11-Diene 12-Monooxygenase identified by improved production of artemisinic acid when expressed from a weak promoter in 96-well plates with hydrophobic overlay were found to outperform parent strain (WT P450) in 96-well plates without hydrophobic overlay.

Figure 7:
FIG. 7 is a graph showing that yeast strains expressing improved *Amorpha*-4,11-diene 12-monooxygenase mutants from strong promoters produce similar concentrations of artemisinic acid to a strain expressing the parental *Amorpha*-4,11-diene 12-monooxygenase from strong promoters when grown in the presence of a hydrophobic overlay (20% isopropyl myristate), but produce significantly more artemisinic acid than the strain expressing parental *Amorpha*-4,11-diene 12-monooxygenase when grown in the absence of hydrophobic overlay in microtiter plates.

Improved *Amorpha*-4,11,-Diene 12-Monooxygenase variants identified from the low-expression screening strain and ported into our high-expression production background were also tested in 96-well microtiter plates without overlay. The P450 variants Y49851 (E128N) and combinatorial variant Y49841 (A8D, F228Y) were compared to an isogenic strain expressing the wild-type P450 (Y26454). Although titers are fairly similar when measured for strains grown with hydrophobic overlay, significant improvements over the isogenic wild type strain can be seen when grown without overlay (FIG. 7).

Combinatorial mutant variants of *Amorpha*-4,11-Diene 12-Monooxygenase identified by improved production of artemisinic acid when expressed from a weak promoter in 96-well plates produce higher concentrations of AA compared to the parental strain (with WT P450) in overlay tanks when expressed from strong promoters.

Figure 8:
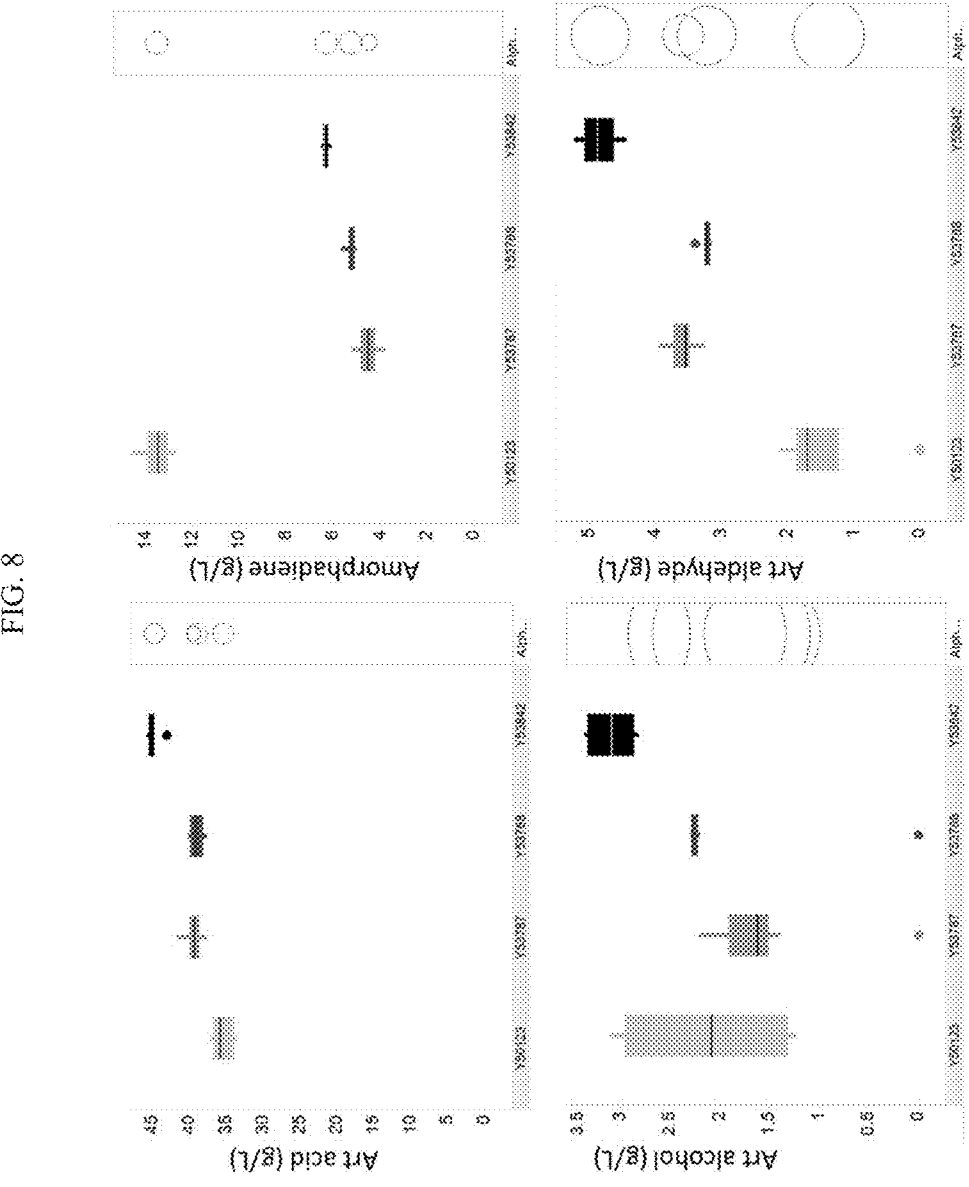
FIG. 8 shows production of artemisinic acid, artemisinic aldehyde, artemisinic alcohol and amorphadiene in fed-batch fermentations by strains expressing improved *Amorpha*-4,11-diene 12-monooxygenase combinatorial mutants identified by screening from low-expression promoters in 96-well plates (Y53787, Y53788, and Y53842) or an isogenic strain expressing the wild-type P450 (Y50123). The strains shown are expressing the combinatorial mutation/wild-type *Amorpha*-4,11-diene 12-monooxygenase genes from strong promoters.

Three top combinatorial mutant variants of *Amorpha*-4,11-Diene 12-Monooxygenase identified in Example 6 were run in fermentation tanks with hydrophobic overlay. When compared to an isogenic strain expressing the wild-type *Amorpha*-4,11-Diene 12-Monooxygenase, yields and productivities for all three mutant variants were higher/artemisinic acid and artemisinic aldehyde titers (oxidized product downstream of the P450) increased, while amorphadiene titers decreased (FIG. 8). When these same strains were run in the 96-well plate model, no significant difference in artemisinic acid titers was detected (FIG. 6).

TABLE 2

Activities of Combinatorial Mutations

| Production Strain | % of wild type titers | Mutations |
|---|---|---|
| Y53843 | 104 | A8D, I94V, E128N, V219, T240N, L350F, Q449K |
| Y53844 | 110 | A8D, I94V, E128N, V219I, T240N, L333M, L350F, Q449K |
| Y54288 | 86 | A8D, E128N, V219I, L350F, Q449K |
| Y54289 | 109 | A8D, I94V, E128N, V219I, T240N, L350F, Q445K |
| Y54290 | 105 | A8D, E128N, V219I, L350F, Q449K |
| Y54291 | 104 | A8D, I94V, E128N, V219I, L333M, A442K, Q449K |
| Y54292 | 105 | A8D, I94V, E128N, V219I, L333M, L350F |
| Y54293 | 105 | A8D, I94V, E128N, L333M, L350F, Q449K |
| Y54294 | 106 | A8D, I94V, E128N, L350F, A442S |
| Y54295 | 105 | A8D, I94V, E128N, V219I, L350F, T420R |
| Y54296 | 107 | A8D, I94V, E128N, T240N, Q449K |
| Y53787 | 112 | A8D, I94V, E128N, V219I, T240N, Q449K |
| Y54297 | 99.2 | A8D, I94V, E128N, T240N, L333M, L350F, T420R |
| Y54298 | 108.5 | A8D, E128N, V219I, T240N, L333M |
| Y53788 | 115 | A8D, I94V, E128N, V219I, T420R |
| Y54299 | 107 | A8D, I94V, E128N, V219I, T240N, L350F, A442K |
| Y53789 | 115 | A8D, I94V, E128N, V219I, L330M, T420R, Q449K |
| Y54300 | 102 | A8D, I94V, E128N, V219I, T241N, L333M |
| Y53842 | 109 | A8D, I94V, E128N, V219I, T241N, L333M, L350F, Q449K |
| Y54302 | 108 | A8D, I94V, E128N, L333M, L350F, Q449K |
| Y54303 | 107 | A8D, I94V, E128N, L350F, Q449K |
| Y54304 | 105 | A8D, I94V, E128N, V219I, T240N, L350F, T420R, Q449K |
| Y54305 | 103 | A8D, I94V, E128N, V219I, L333M |
| Y54306 | 107 | A8D, I94V, E128N, L350F, Q449K |

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

For example, in addition to the compositions and methods disclosed above, the invention features the subject matter recited in the following enumerated embodiments.

Exemplary Enumerated Embodiments of the Invention

Embodiment 1. A variant *Amorpha*-4,11-diene 12-monooxygenase polypeptide having an amino acid sequence that differs from the amino acid sequence of SEQ ID NO: 1 by way of one or more amino acid substitutions.

Embodiment 2. The variant polypeptide of embodiment 1, wherein the one or more amino acid substitutions comprise A8D, 194L, 194V, E128N, R172I, V219I, T240N, K244C, L333M, Q345K, L350F, T420R, A442K, A442S, Q449K, S468C, T486C, L489C, and/or V491 M.

Embodiment 3. The variant polypeptide of embodiment 1 or 2, wherein the one or more amino acids substitutions comprise A8D, 194V, E128N, V219I, T240N, L350F, and/or Q449K, optionally wherein the one or more amino acids substitutions comprise A8D, 194V, E128N, V219I, T240N, L350F, and Q449K.

Embodiment 4. The variant polypeptide of embodiment 1 or 2, wherein the one or more amino acid substitutions comprise A8D, 194V, E128N, V219I, T240N, L333M, L350F, and/or Q449K, optionally wherein the one or more amino acid substitutions comprise A8D, 194V, E128N, V219I, T240N, L333M, L350F, and Q449K.

Embodiment 5. The variant polypeptide of embodiment 1 or 2, wherein the one or more amino acid substitutions comprise A8D, E128N, V219I, L350I, and/or Q449K, optionally wherein the one or more amino acid substitutions comprise A8D, E128N, V219I, L350I, and Q449K.

Embodiment 6. The variant polypeptide of embodiment 1 or 2, wherein the one or more amino acid substitutions comprise A8D, E128N, V219I, L350F, and/or Q449K, optionally wherein the one or more amino acid substitutions comprise A8D, E128N, V219I, L350F, and Q449K.

Embodiment 7. The variant polypeptide of any one of embodiments 1 to 6, wherein the amino acid sequence of the variant polypeptide is at least 90% identical (e.g., at least 90%, 91%, 92%, 93%, 94%, 95%, 96%, 97%, 98%, or 99% identical, or more) to the amino acid sequence of SEQ ID NO: 1, optionally wherein the amino acid sequence of the variant polypeptide is at least 95% identical to the amino acid sequence of SEQ ID NO: 1, optionally wherein the amino acid sequence of the variant polypeptide is at least 96% identical to the amino acid sequence of SEQ ID NO: 1, optionally wherein the amino acid sequence of the variant polypeptide is at least 97% identical to the amino acid sequence of SEQ ID NO: 1, optionally wherein the amino acid sequence of the variant polypeptide is at least 98% identical to the amino acid sequence of SEQ ID NO: 1, optionally wherein the amino acid sequence of the variant polypeptide is at least 99% identical to the amino acid sequence of SEQ ID NO: 1.

Embodiment 8. The variant polypeptide of any one of embodiments 1 to 7, wherein the amino acid sequence of the variant polypeptide differs from the amino acid sequence of SEQ ID NO: 1 only by way of the one or more amino acid substitutions.

Embodiment 9. A nucleic acid encoding the polypeptide of any one of the preceding embodiments.

Embodiment 10. A host cell comprising the polypeptide of any one of embodiments 1 to 8.

Embodiment 11. A host cell comprising the nucleic acid of embodiment 9.

Embodiment 12. The host cell of embodiment 10 or 11, wherein the host cell is capable of producing a compound selected from artemisinic alcohol, artemisinic aldehyde, and artemisinic acid.

Embodiment 13. The host cell of embodiment 12, wherein the host cell is capable of producing artemisinic acid.

Embodiment 14. The host cell of any one of embodiments 10 to 13, further comprising a nucleic acid encoding a polypeptide selected from *Artemisia annua* ADH1 and *Artemisia annua* ALDH1.

Embodiment 15. A method of generating a variant of a target p450 enzyme comprising:

- obtaining a library of nucleic acids encoding variants of the target p450;
- transforming a population of host cells with the library such that each library nucleic acid is operably linked to a weak promoter;
- plating individual transformed host cells into individual wells of a multi-well plate;
- culturing the host cells under conditions that produce a test compound;
- measuring the level of test compound produced by the transformed host cells; and
- selecting variants that increase the level of the test compound relative to a control.

Embodiment 16. The method of embodiment 15, wherein the weak promoter is selected from pGAL10, pGAL2, pGAL1_v22, pGAL1_v25, pGAL1_v2, pGAL3, and pGAL2_v22.

Embodiment 17. The method of embodiment 15 or 16, wherein the test compound is an isoprenoid.

Embodiment 18. The method of embodiment 17, wherein the test compound is selected from hemiterpenes, monoterpenes, sesquiterpenes, diterpenes, triterpenes, sesterterpenoids, and carotenoids.

Embodiment 19. The method of embodiment 18, wherein the test compound is selected from artemisinic alcohol, artemisinic aldehyde, and artemisinic acid.

Embodiment 20. The method of embodiment 15 or 16, wherein the test compound is a meroterpenoids.

Embodiment 21. The method of any of the preceding embodiments, wherein the target p450 enzyme is *Amorpha*-4,11-diene 12-monooxygenase.

Embodiment 22. The method of any one of the preceding embodiments, further comprising:

- creating a second library of nucleic acids encoding variants of the target p450, wherein the nucleic acids comprise combinations of the selected variants;
- transforming a population of host cells with the second library such that each second library nucleic acid is operably linked to a second weak promoter;
- plating individual transformed host cells into individual wells of a multi-well plate;

culturing the host cells under conditions that produce the test compound;

measuring the level of test compound produced in each well of the multi-well plate; and selecting second order variants that increase the level of the test compound relative to a second control.

Embodiment 23. The method of embodiment 22, wherein the second weak promoter is distinct from the weak promoter.

Embodiment 24. The method of embodiment 22, wherein the second weak promoter is identical to the weak promoter.

Embodiment 25. The method of embodiment 22, wherein the second control is distinct from the control.

Embodiment 26. The method of embodiment 22, wherein the second control is identical to the control.

Embodiment 27. The method of embodiment 22, wherein the second library comprises nucleic acids encoding all possible combinations of the selected variants.

SEQUENCE APPENDIX

*Artemisia annua* Amorpha-4,11-diene 12-monooxygenase (SEQ ID NO: 1)

KSILKAMALSLTTSIALATILLFVYKFATRSKSTKKSLPEPWRLPIIGH

MHHLIGTTPHRGVRDLARKYGSLMHLOLGEVPTIVVSSPKWAKEILTTYD

ITFANRPETLTGEIVLYHNTDVVLAPYGEYWRQLRKICTLELLSVKKVKS

FQSLREEECWNLVQEIKASGSGRPVNLSENVFKLIATILSRAAFGKGIKD

QKELTEIVKEILRQTGGFDVADIFPSKKFLHHLSGKRARLTSLRKKIDNL

IDNLVAEHTVNTSSKTNETLLDVLLRLKDSAEFPLTSDNIKAIILDMFGA

GTDTSSSTIEWAISELIKCPKAMEKVQAELRKALNGKEKIHEEDIQELSY

LNMVIKETLRLHPPLPLVLPRECRQPVNLAGYNIPNKTKLIVNVFAINRD

PEYWKDAEAFIPERFENSSATVMGAEYEYLPFGAGRRMCPGAALGLANVQ

LPLANILYHFNWKLPNGVSYDQIDMTESSGATMQRKTELLLVPSF

*Artemisia annua* ADH1

(SEQ ID NO: 2)

MAQKAPGVITCKAAVVWESSGPVVLEEIRVDPPKASEVRIKMLCASLCHT

DVLCTKGFPIPLFPRIPGHEGVGVIESIGKDAKGLKPGDIVMPLYLGECG

QCLNCKTGKTNLCHVYPPSFSGLMNDGTSRMSIARTGESIYHFASCSTWT

EYAVADCNYVLKINPKISYPHASFLSCGFTTGFGATWRETQVSKGSSVAV

FGIGTVGLGVIKGAQLQGASKIIGVDVNQYKAAKGKVFGMTDFINPKDHP

DKSVSELVKELTHGLGVDHCFECTGVPSLLNEALEASKIGIGTVVPIGAG

GEASVAINSLILFSGRTLKFTAFGGVRTQSDLPVIIDKCLNKEIQLDELL

THEIHLDNIQEAFEILKKPDCVKILIKF

*Artemisia annua* ALDH1

(SEQ ID NO: 3)

MSSGANGSSKSASHKIKFTKLFINGEFVDSISGNTFDTINPATEEVLATV

AEGRKEDIDLAVKAAREAFDNGPWPRMSGEARRKIMLKFADLIDENADEL

TTLEVIDGGKLFGPVRHFEVPVSSDTFRYFAGAADKIRGATLKMSSNIQA

YTLREPIGVVGHIIPWNGPAFMFATKVAPALAAGCTMVIKPAEHTPLTVL

FLAHLSKLAGVPDGVINVVNGFGKTAGAAVSSHMDIDMVTFTGSTEVGRT

VMQAAALSNLKPVSLELGGKSPLIVFDDADVDKAAEFAILGNFTNKGEMC

VAGSRVFVQEGIHDVFVKKLEGAVKAWATRDPFDLATRHGPQNNKQQYDK

VLSCINHGKKEGATLVTGGKPFGKKGYYIEPTLFTNVTDDMTSAKEEIFG

PVISVLKFKTVEEVIKRANATKYGLASGVFTKNIDVVNTVSRSLRAGAVW

VNCYLALDRDAPHGGYKMSGFGREQGLEALEHYLQIKTVATPIYDSPWL

*Artemisia annua* ADS (SEQ ID NO: 4)

MSLTEEKPIRPIANFPPSIWGDQFLIYEKQVEQGVEQIVNDLKKEVRQLLKEALDIPMKHANLLKLIDEI

QRLGIPYHFEREIDHALQCIYETYGDNWNGDRSSLWFRLMRKQGYYVTCDVFNNYKDKNGAFKQSLAN

-continued

DV EGLLELYEATSMRVPGEIILEDALGFTRSRLSIMTKDAFSTNPALFTEIQRALKQPLWKRLPRIEAAQYI

PFYQQQDSHNKTLLKLAKLEFNLLQSLHKEELSHVCKWWKAFDIKKNAPCLRDRIVECYFWGLGSGYEP

QYSRARVFFTKAVAVITLIDDTYDAYGTYEELKIFTEAVERWSITCLDTLPEYMKPIYKLFMDTYTEMEEF

LAKEGRTDLFNCGKEFVKEFVRNLMVEAKWANEGHIPTTEEHDPVVIITGGANLLTTTCYLGMSDIFTKE

SVEWAVSAPPLFRYSGILGRRLNDLMTHKAEQERKHSSSSLESYMKEYNVNEEYAQTLIYKEVEDVWKDI

NREYLTTKNIPRPLLMAVIYLCQFLEVQYAGKDNFTRMGDEYKHLIKSLLVYPMSI

---

What is claimed:

1. A variant *Amorpha*-4,11-diene 12-monooxygenase polypeptide comprising the amino acid sequence of SEQ ID NO:1 comprising one or more amino acid substitutions selected from A8D, E128N, R172I, V219I, T240N, K244C, F282N, L333M, Q345K, L350F, T420R, A442K, A442S, Q449K, S468C, T486C, L489C, and V491 M.

2. A nucleic acid encoding the polypeptide of claim 1.

3. A host cell comprising the polypeptide of claim 1.

4. A host cell comprising the nucleic acid of claim 2.

5. The host cell of claim 3, wherein the host cell is capable of producing a compound selected from artemisinic alcohol, artemisinic aldehyde, and artemisinic acid.

6. The host cell of claim 5, wherein the host cell is capable of producing artemisinic acid.

7. The host cell of claim 3, further comprising a nucleic acid encoding a polypeptide selected from *Artemisia annua* alcohol dehydrogenase 1 (ADH1) and *Artemisia annua* aldehyde dehydrogenase 1 (ALDH1).

8. The variant polypeptide of claim 1, wherein the one or more amino acids substitutions are selected from A8D, E128N, V219I, T240N, L350F, and Q449K.

9. The variant polypeptide of claim 1, wherein the one or more amino acid substitutions are selected from A8D, E128N, V219I, T240N, L333M, L350F, and Q449K.

10. The variant polypeptide of claim 1, wherein the one or more amino acid substitutions are selected from A8D, E128N, V219I, L350F, and Q449K.

11. The variant polypeptide of claim 1, wherein the one or more amino acid substitutions comprise V219I, F282N, or A442K.

12. The variant polypeptide of claim 1, wherein the one or more amino acid substitutions comprise A8D or E128N.

* * * * *